(12) United States Patent
Ho et al.

(10) Patent No.: US 12,122,048 B2
(45) Date of Patent: Oct. 22, 2024

(54) HIGH STIFFNESS BAR WITH INTERNAL ACTUATORS AND INTERNAL CABLING

(71) Applicant: Auris Health, Inc., Redwood City, CA (US)

(72) Inventors: Alvin Z. Ho, San Mateo, CA (US); Nicholas J. Eyre, Redwood City, CA (US); Colin Allen Wilson, Burlingame, CA (US); Sven Wehrmann, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 18/094,299

(22) Filed: Jan. 6, 2023

(65) Prior Publication Data

US 2023/0226684 A1    Jul. 20, 2023

Related U.S. Application Data

(60) Provisional application No. 63/297,236, filed on Jan. 7, 2022.

(51) Int. Cl.
| | |
|---|---|
| *A61B 34/30* | (2016.01) |
| *B25J 5/00* | (2006.01) |
| *B25J 9/12* | (2006.01) |
| *B25J 18/00* | (2006.01) |

(52) U.S. Cl.
CPC ............... *B25J 9/123* (2013.01); *A61B 34/30* (2016.02); *B25J 5/007* (2013.01); *B25J 18/00* (2013.01)

(58) Field of Classification Search
None
See application file for complete search history.

(56) References Cited

U.S. PATENT DOCUMENTS

| | | | | |
|---|---|---|---|---|
| 3,541,334 | A * | 11/1970 | Sobolewski | A61B 6/56 378/197 |
| 4,972,852 | A * | 11/1990 | Koob | A61B 6/0487 5/943 |
| 10,888,386 | B2 * | 1/2021 | Eyre | A61G 13/08 |
| 11,175,596 | B2 * | 11/2021 | Nienhuys | B01D 45/08 |

* cited by examiner

*Primary Examiner* — Bobby Rushing, Jr.
(74) *Attorney, Agent, or Firm* — Frost Brown Todd LLP

(57) ABSTRACT

A surgical system may include an elongated arm support and a robotic arm supported on the elongated arm support. The robotic arm may translate along the elongated arm support. A partially enclosed cavity may be defined in the elongated arm support for receiving an electrical cable electrically coupled to the robotic arm so that the first electrical cable is within the cavity and includes a rolling loop that moves in conjunction with movement of the robotic arm.

14 Claims, 23 Drawing Sheets

HIGH STIFFNESS BAR WITH INTERNAL ACTUATORS AND INTERNAL CABLING

CROSS-REFERENCE TO RELATED APPLICATION(S)

This application claims the benefit of U.S. Provisional App. No. 63/297,236, filed on Jan. 7, 2022, which is hereby incorporated by reference in its entirety.

TECHNICAL FIELD

The systems and methods disclosed herein are directed to beams for supporting robotic arms, and more particularly to robotic medical systems with high stiffness beams for supporting robotic arms.

BACKGROUND

A robotically enabled medical system is capable of performing a variety of medical procedures, including both minimally invasive procedures, such as laparoscopy, and non-invasive procedures, such as endoscopy (e.g., bronchoscopy, ureteroscopy, gastroscopy, etc.).

Such robotic medical systems may include robotic arms configured to control the movement of medical tool(s) during a given medical procedure. In order to achieve a desired pose of a medical tool, a robotic arm may be placed into a particular pose during a set-up process or during teleoperation.

SUMMARY

Some robotically enabled medical systems may include an arm support (e.g., a bar) that is connected to respective bases of the robotic arms and supports the robotic arms. For robotic medical systems with bars supporting robotic arms, the stiffness (e.g., bending stiffness and torsional stiffness) of the bars affects the stability of robotic arms. For example, a bar with high stiffness provides high stability to robotic arms supported by the bar, which in turn provides high stability to medical instruments coupled to the robotic arms and allows enhanced precision during robotic medical procedures.

Accordingly, there is a need for a robotic medical system with an arm support having high stiffness.

As disclosed herein, bars with cavities are used so that electrical and mechanical components may be positioned within the cavities. Such bars may require open sections (e.g., C-channels) for placing certain components (e.g., actuators and electrical cables) on the bars. However, open sections (e.g., C-channels) typically have lower torsional stiffness than closed sections (e.g., having fully enclosed cross-sections). Thus, the torsional stiffness of a bar may be increased by reducing a portion of the bar having open sections.

Reducing the portion of the bar having open sections may include placing at least some of the components inside the cavities, which allows increasing the size of a closed section, which increases the torsional stiffness compared to a bar with a small, closed section. This, however, requires providing electrical connections between components located inside the cavities and components located outside the cavities. For example, a robotic arm that can slide along the bar may require an actuator located outside the cavity to control the movement of the robotic arm. The actuator requires an electrical connection for receiving the energy and/or control signals for causing movement, while an opposite end of the electrical connection may be connected to a component (e.g., a power line and/or a control signal line) located inside the cavity. The electrical connection may require an opening (e.g., a slot) in the bar so that the electrical connection can extend from inside the cavity to outside the cavity. Thus, reducing the number and size of the opening may further increase the torsional stiffness of the bar.

Accordingly, the systems and/or methods disclosed herein advantageously improve the stiffness of arm supports (e.g., bars). This leads to a better overall user experience because the user can perform robotic medical procedures accurately and precisely, which, in turn, improves the safety and efficiency of the robotic medical procedures.

The systems, methods and devices of this disclosure each have several innovative aspects, no single one of which is solely responsible for the desirable attributes disclosed herein.

In accordance with some embodiments of the present disclosure, a surgical system includes an elongated arm support and a first robotic arm supported on the elongated arm support. A partially enclosed cavity is defined in the elongated arm support for receiving a first electrical cable electrically coupled to the first robotic arm so that the first electrical cable is within the cavity and includes a first rolling loop that moves in conjunction with movement of the first robotic arm.

In accordance with some embodiments, a surgical system includes an elongated arm support and a robotic arm supported on the elongated arm support. A partially enclosed cavity is defined in the elongated arm support for receiving an actuator and an electrical cable therein so that the electrical cable is within the cavity and includes a rolling loop that moves in conjunction with movement of the robotic arm.

In accordance with some embodiments, a surgical system includes a beam with a partially enclosed cavity defined therein, a first carriage located within the cavity; a second carriage located at least partially outside the cavity; and an actuator located within the cavity. The actuator is mechanically coupled with the first carriage and the second carriage by a band or wire for moving the first carriage and the second carriage. The surgical system also includes a first electrical cable with a rolling loop for electrically coupling the first carriage from a fixed location within the cavity; and a second electrical cable electrically coupling the first carriage and the second carriage.

In accordance with some embodiments, a surgical system includes a joint. The joint includes a chassis with an enclosed cavity and a load-bearing output carriage, which moves relative to the chassis. The joint also includes an electrical cable assembly coupled to both the chassis and the load-bearing output carriage. The electrical cable assembly has a first bend located within the enclosed cavity which moves relative to the chassis as the load-bearing output carriage moves. The electrical cable assembly has a second bend around a redirect surface. The second bend does not move relative to the chassis.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other embodiments of the disclosed concepts are possible, and various advantages can be achieved with the disclosed embodiments. Headings are included herein for reference and to aid in locating various sections. These headings are not intended to limit the scope of the concepts described with respect thereto. Such concepts may have applicability throughout the entire specification.

A. Robotic System—Cart.

Figure 1:
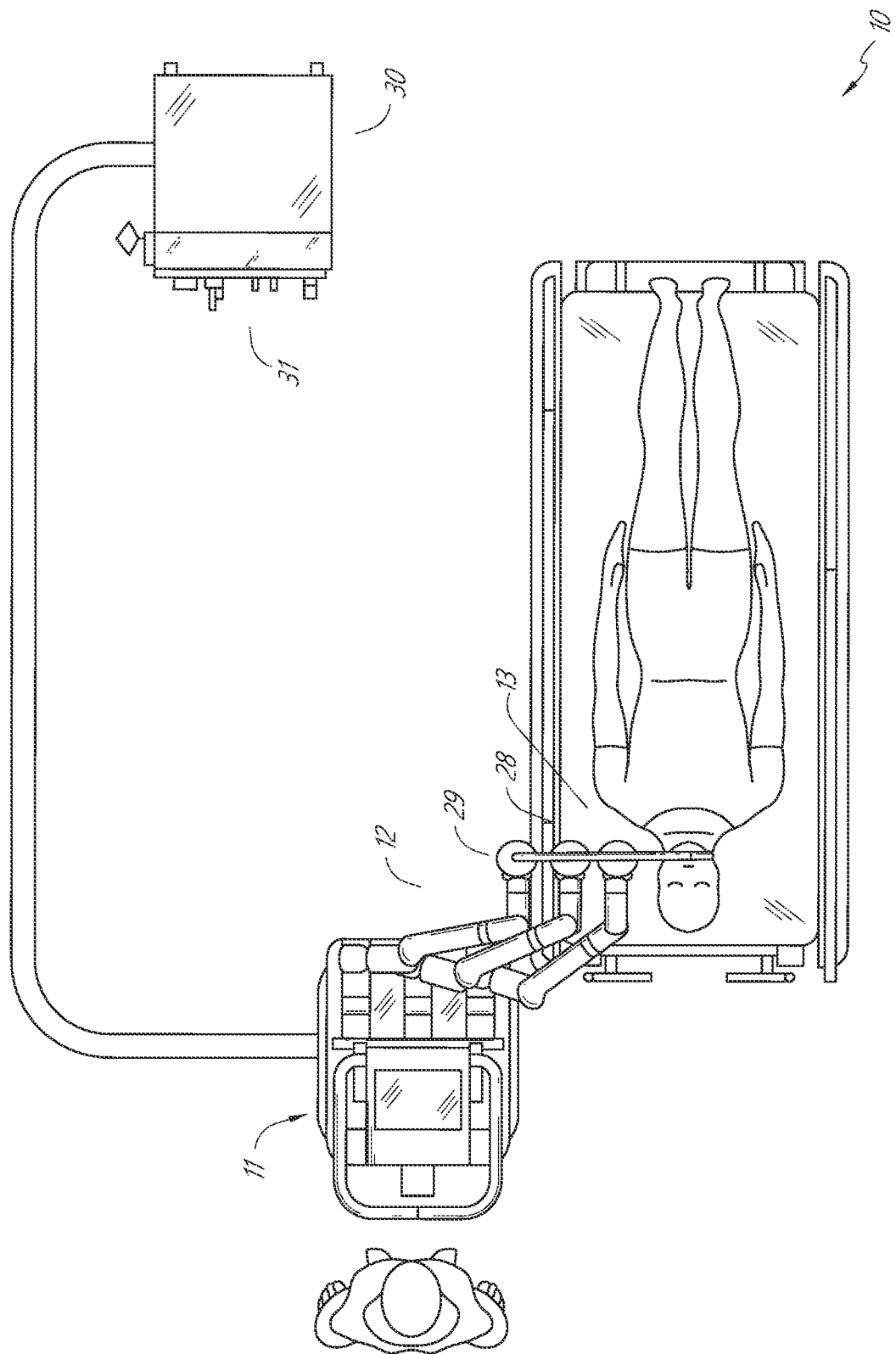
FIG. 1 illustrates an embodiment of a cart-based robotic system arranged for diagnostic and/or therapeutic bronchoscopy procedure(s).
Figure 2:
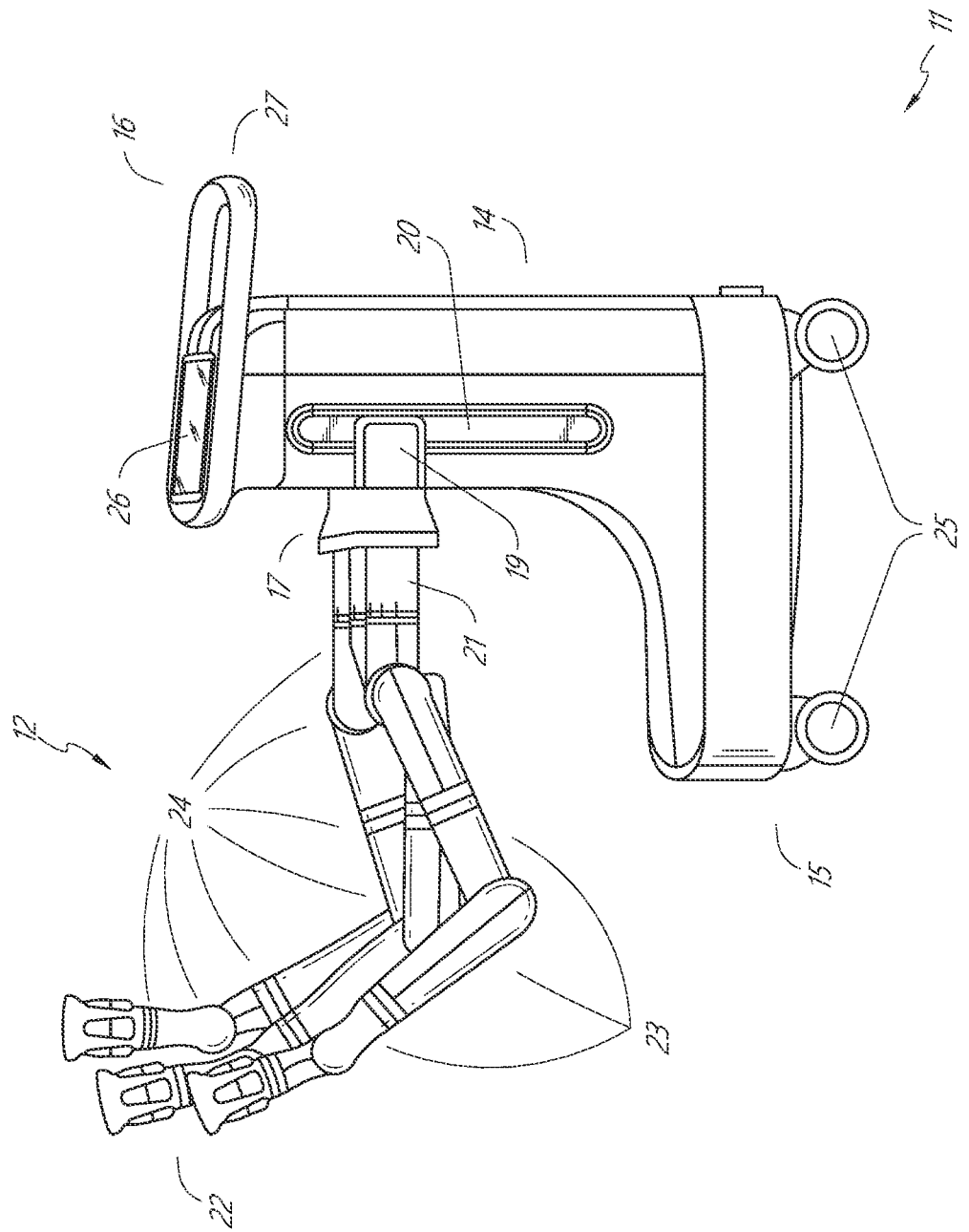
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
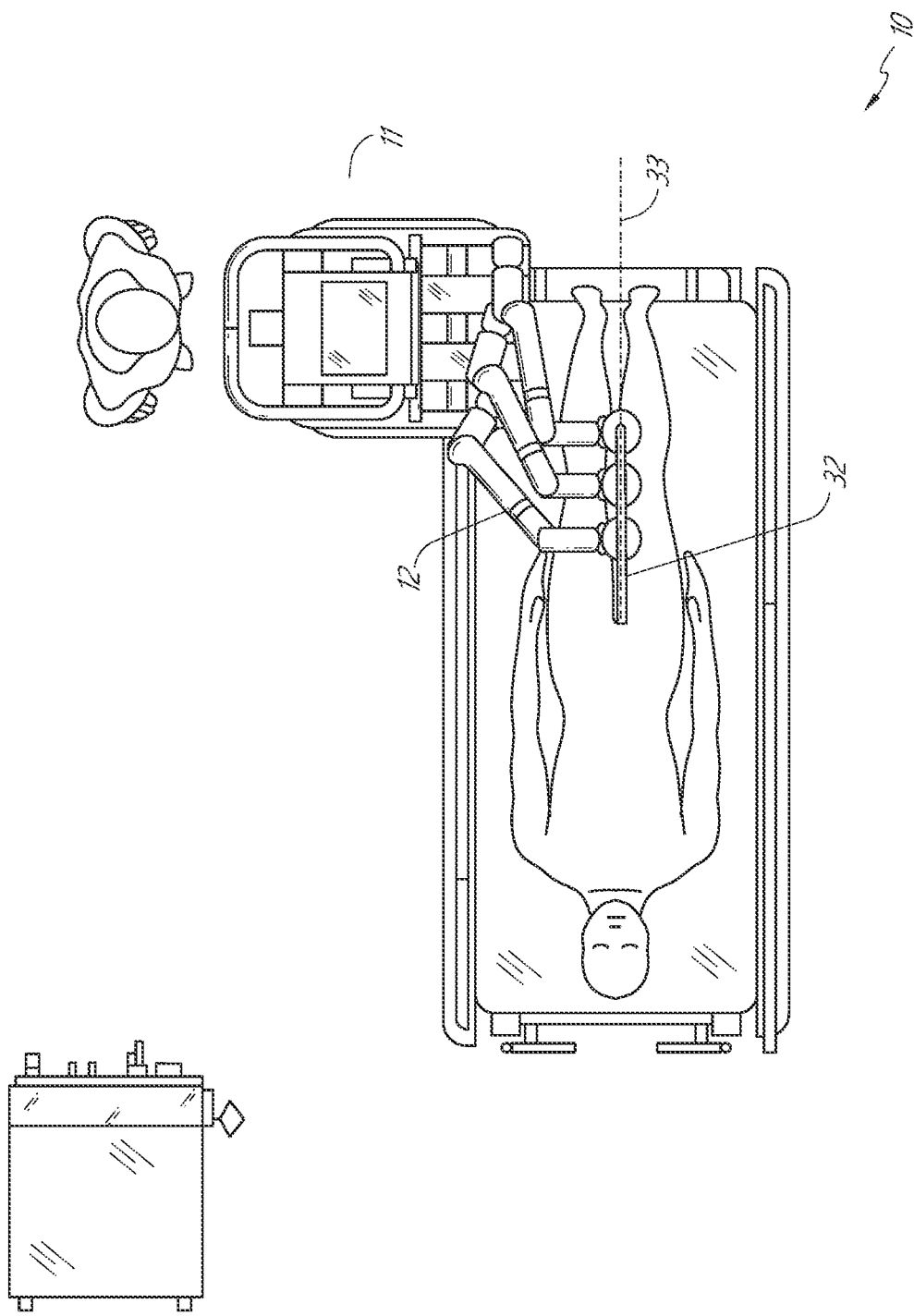
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
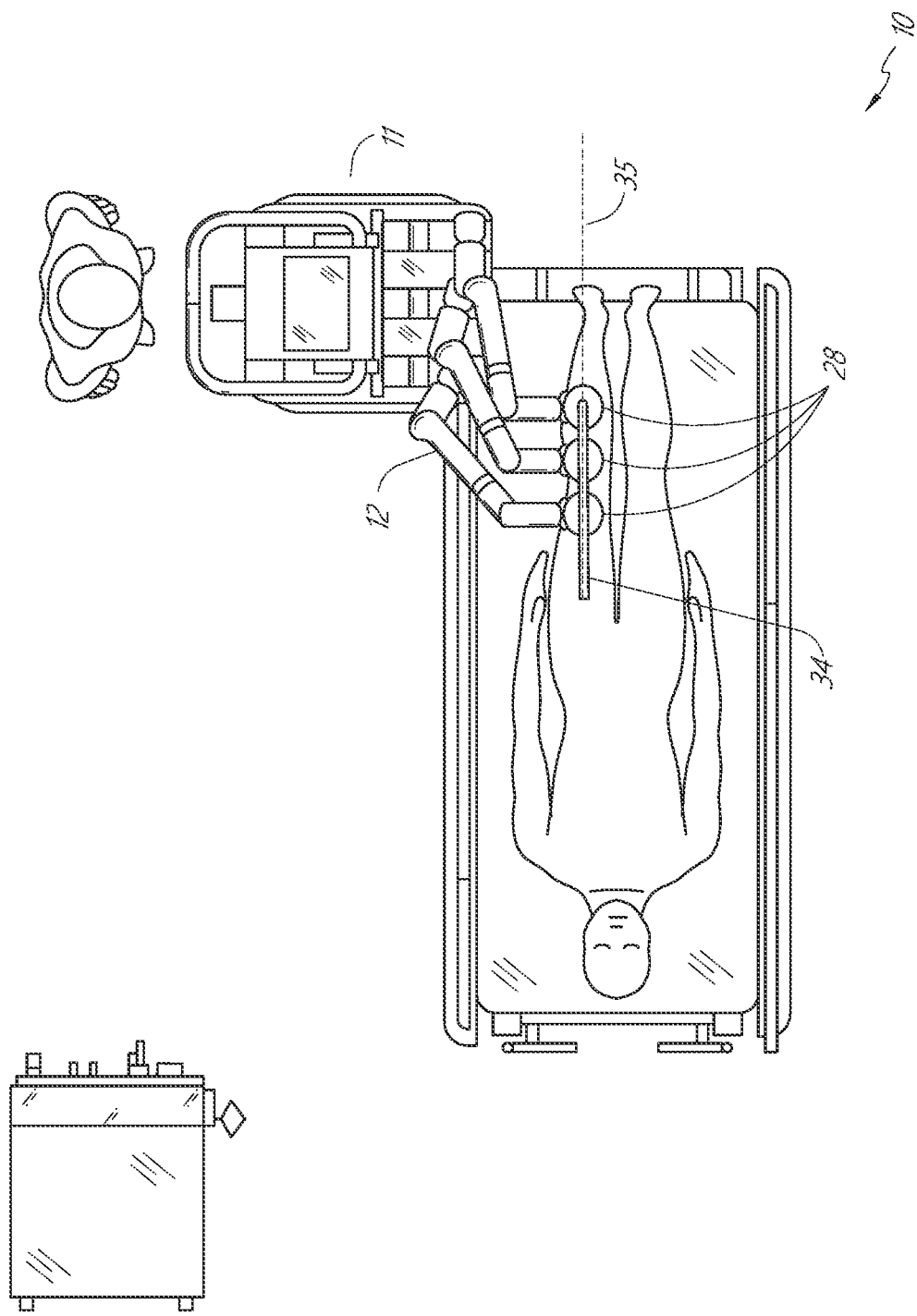
FIG. 4 illustrates an embodiment of the robotic system of FIG. 1 arranged for a vascular procedure.

FIG. 4 illustrates an embodiment of a robotically enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
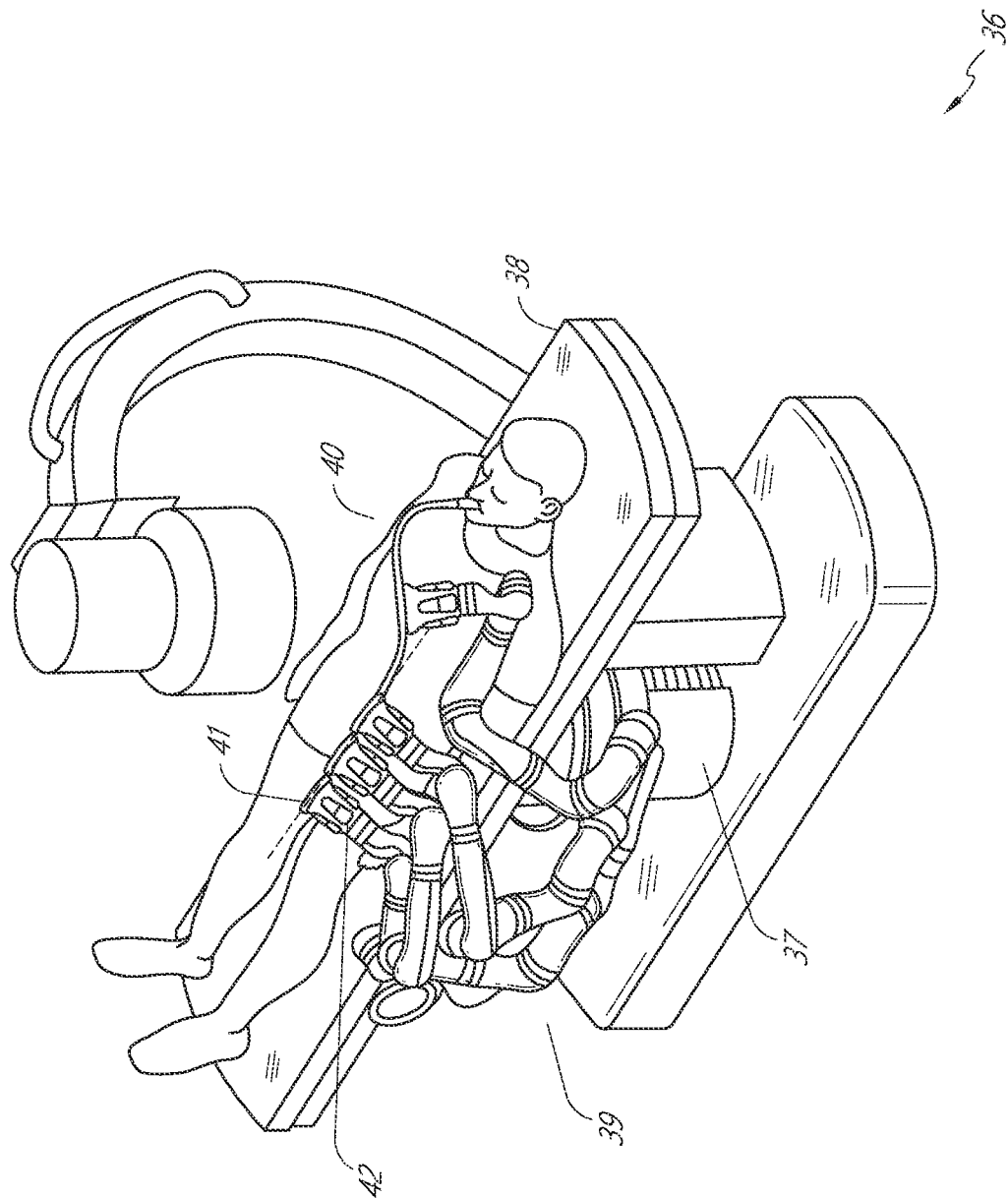
FIG. 5 illustrates an embodiment of a table-based robotic system arranged for a bronchoscopy procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
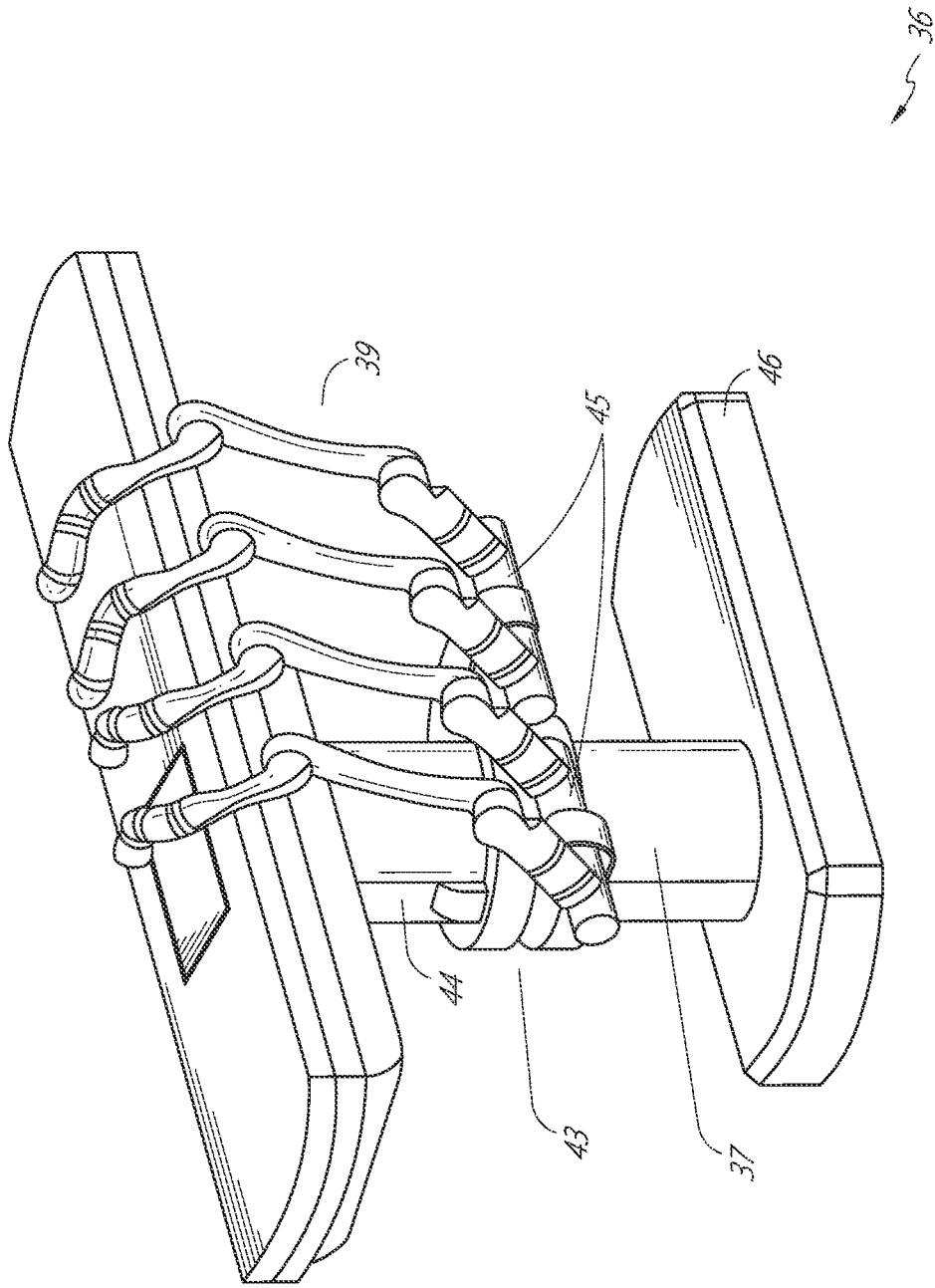
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
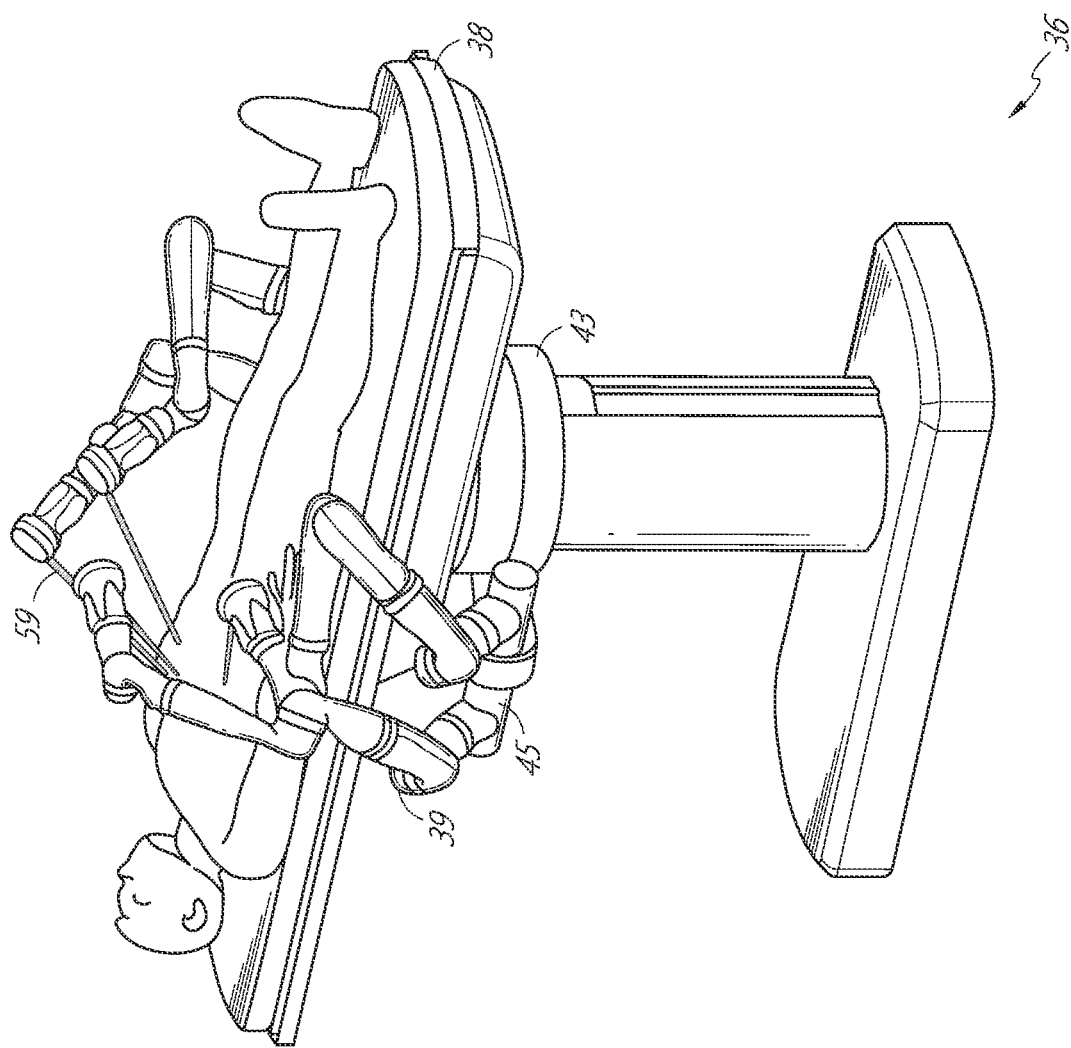
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
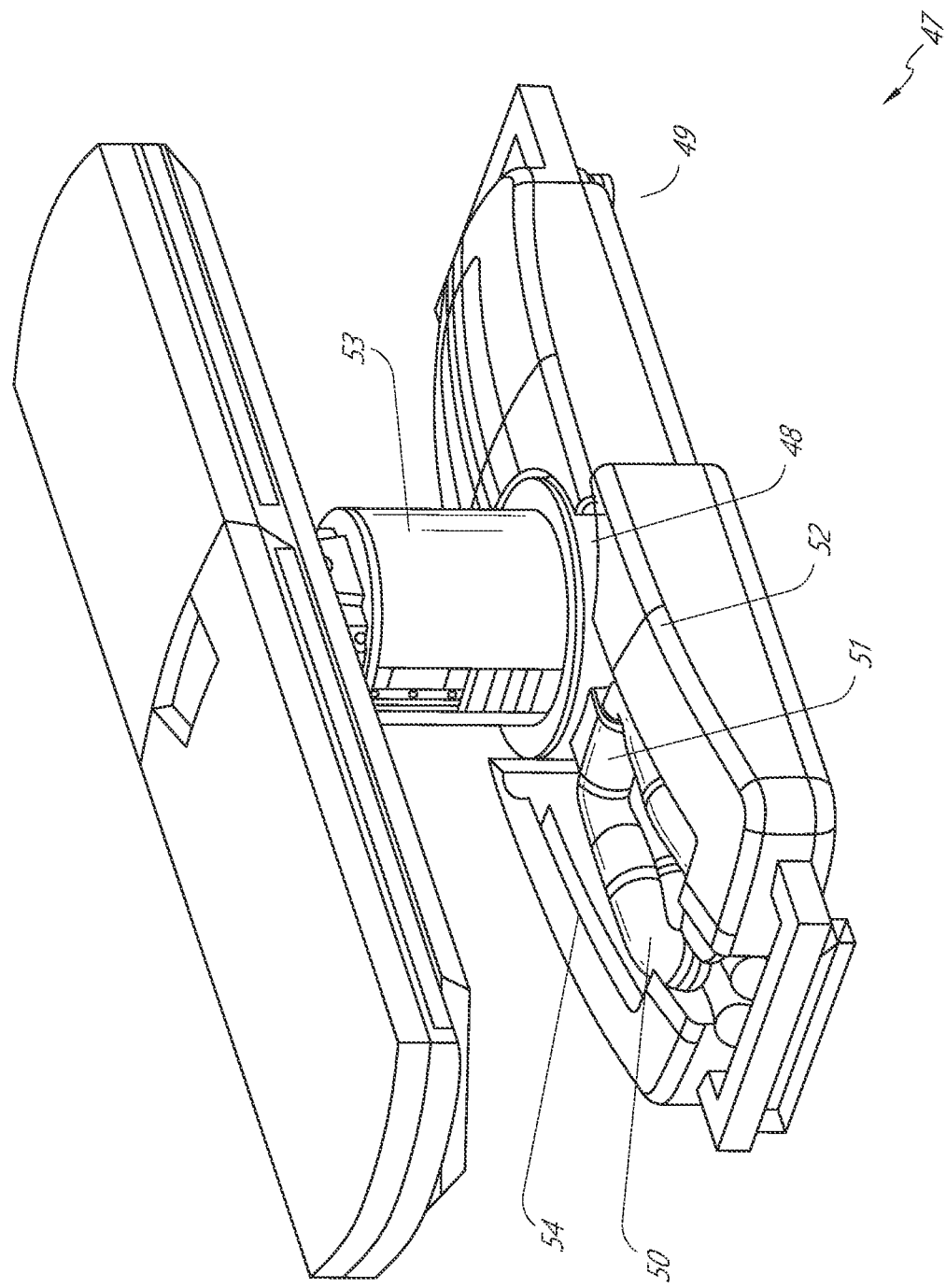
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
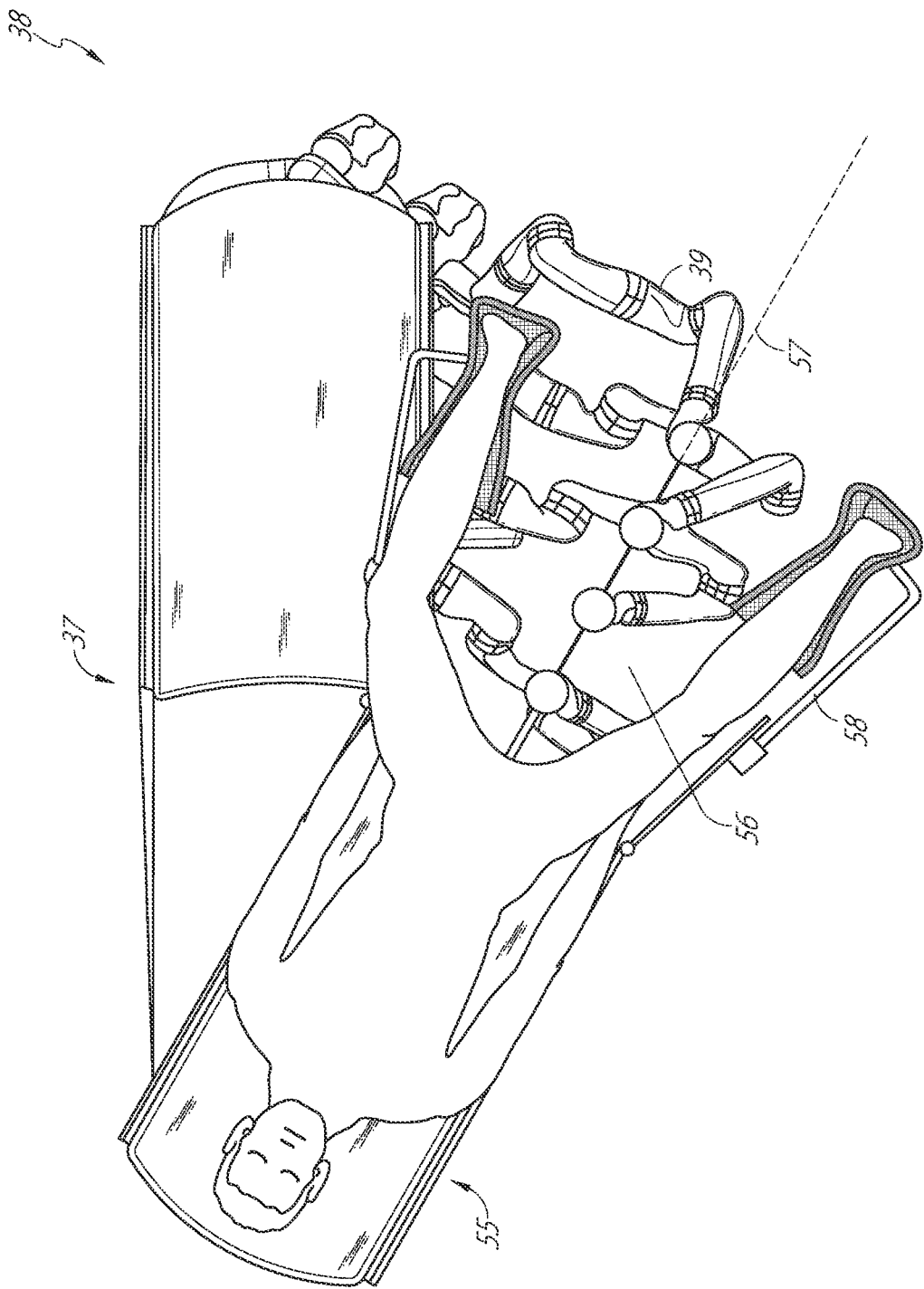
FIG. 8 illustrates an embodiment of a table-based robotic system configured for a ureteroscopy procedure.

FIG. 8 illustrates an embodiment of a robotically enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
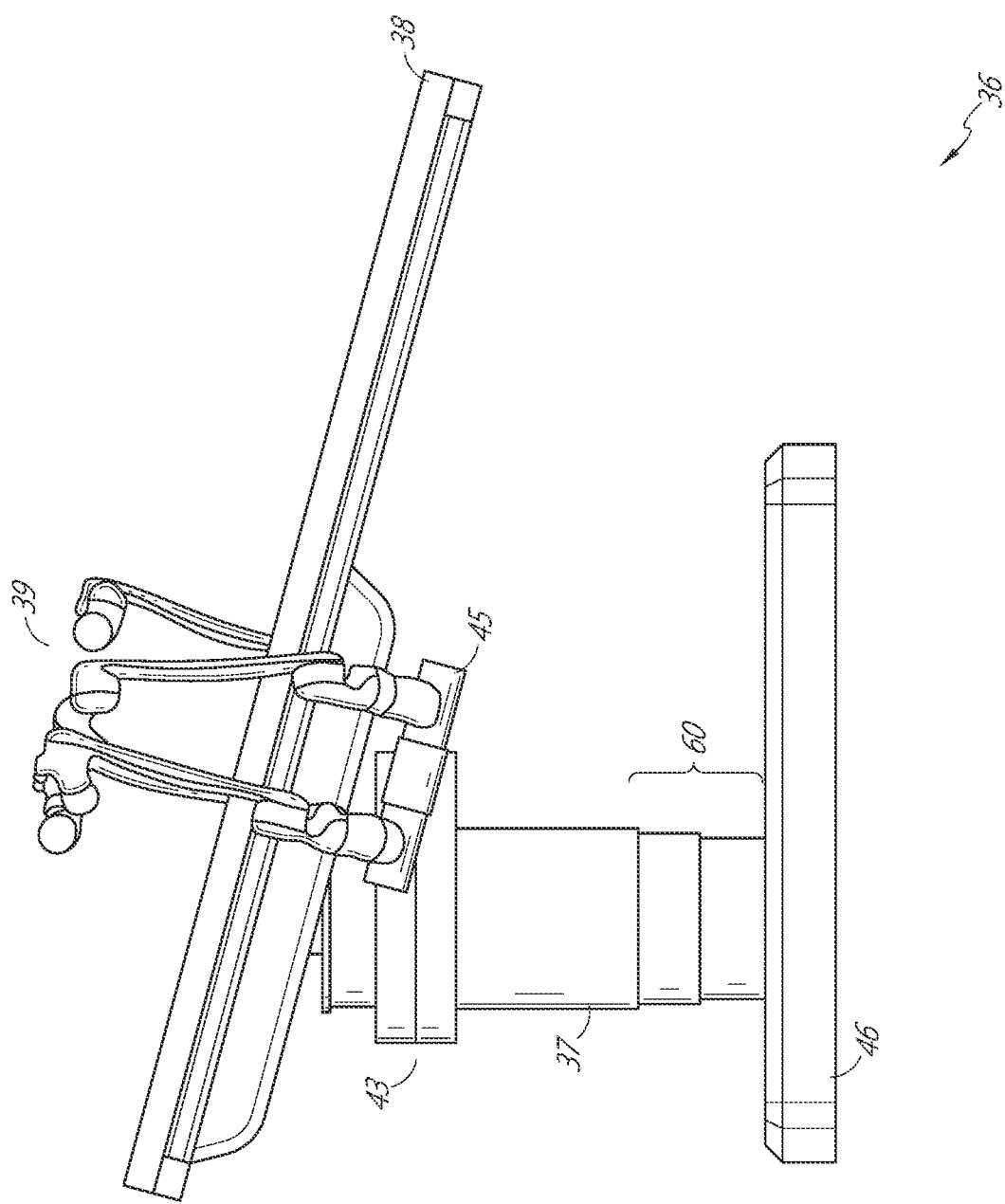
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
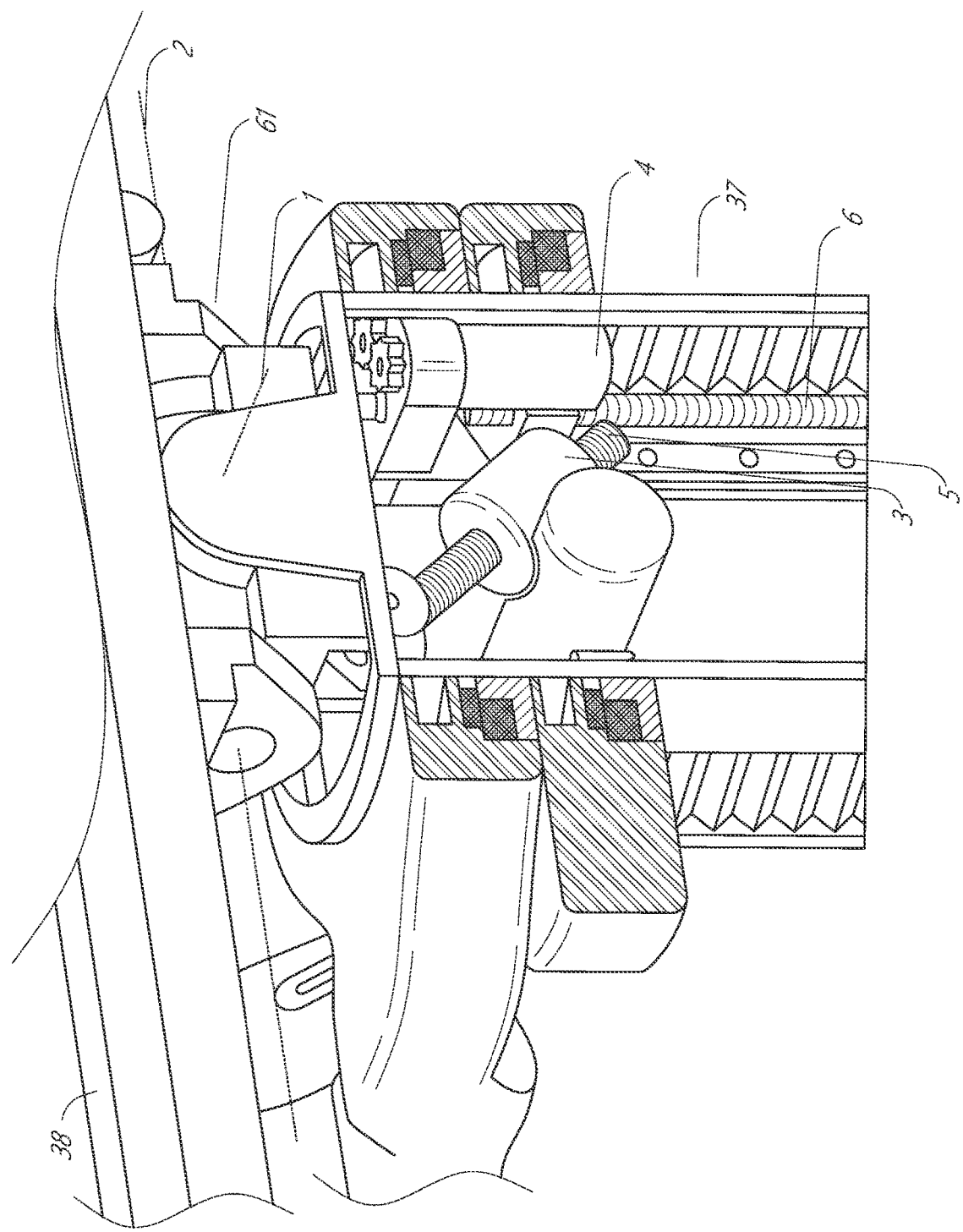
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
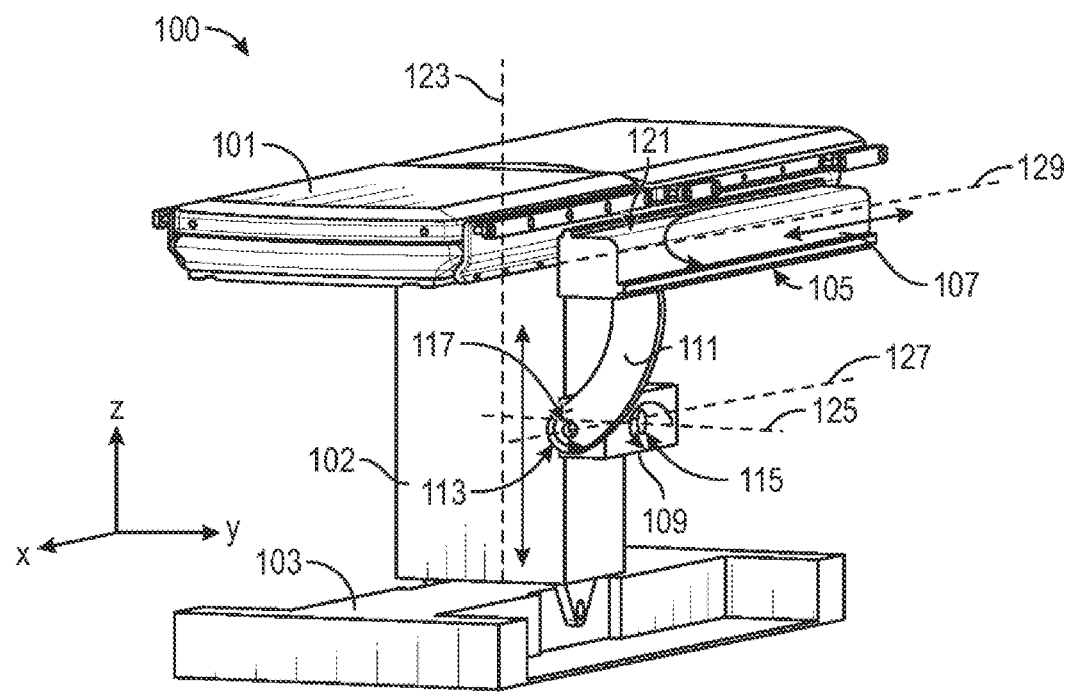
FIG. 12 illustrates an alternative embodiment of a table-based robotic system.
Figure 13:
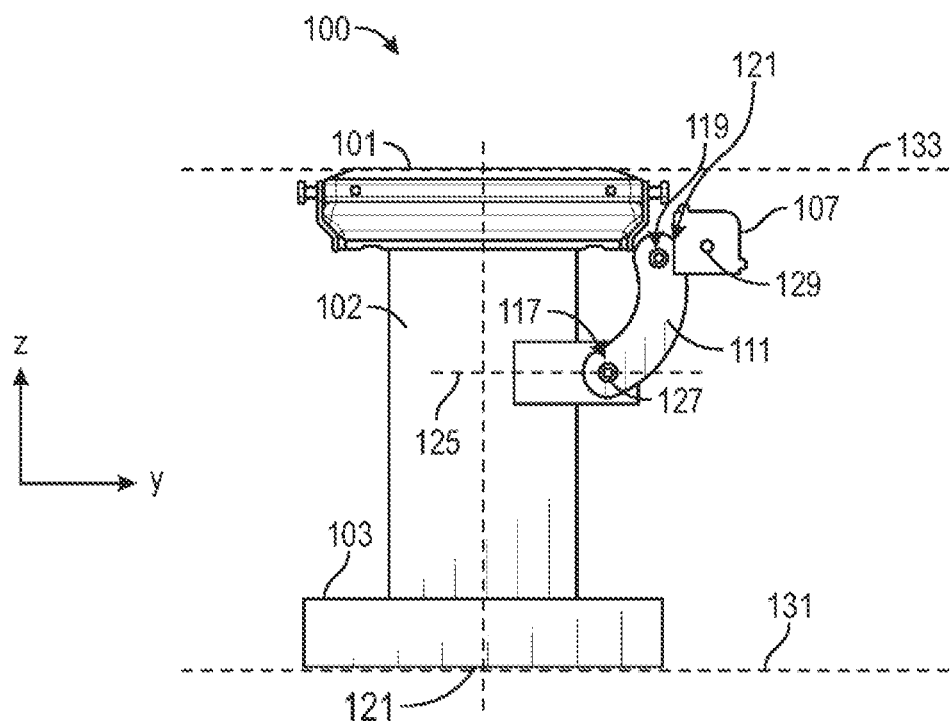
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
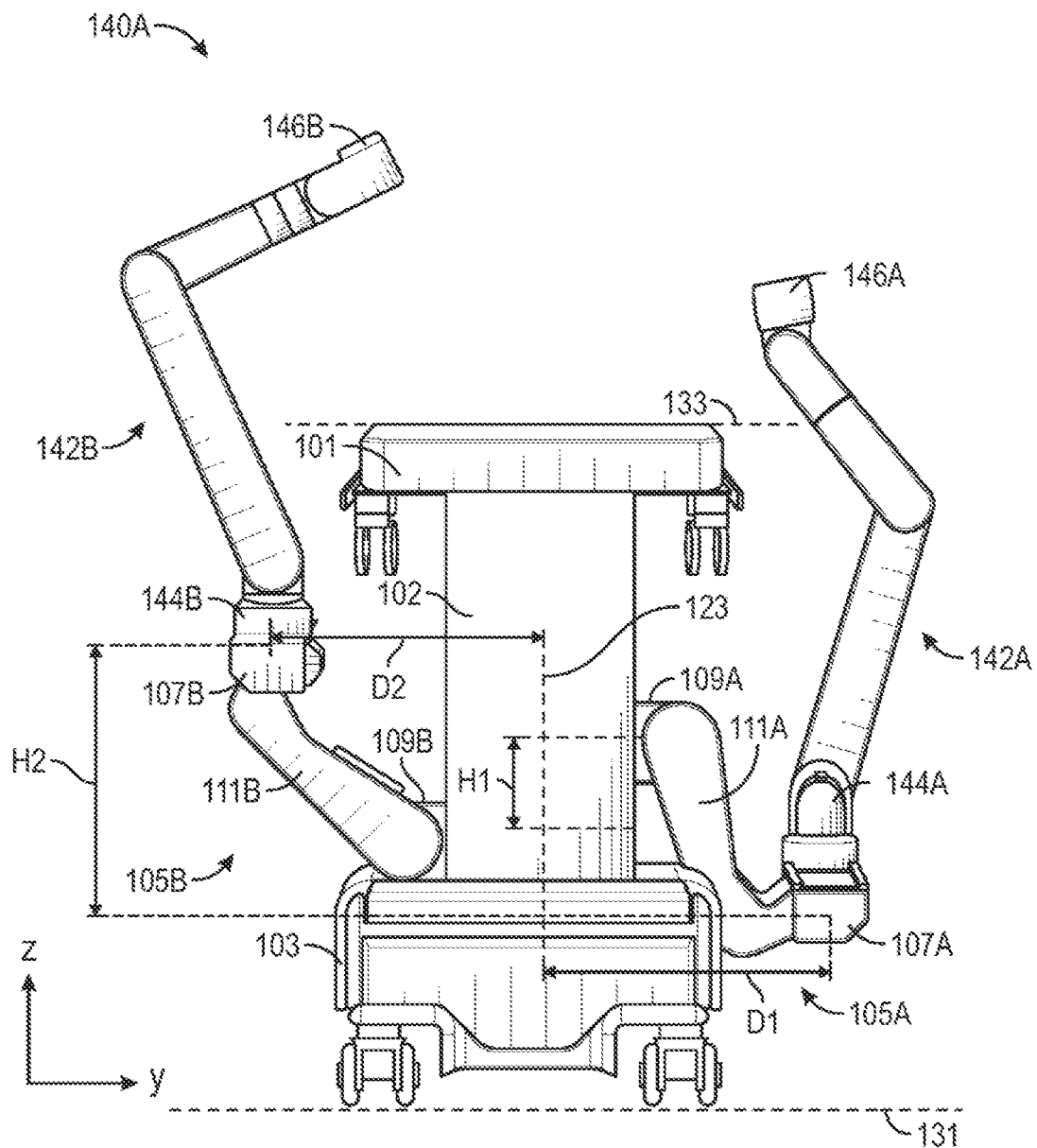
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
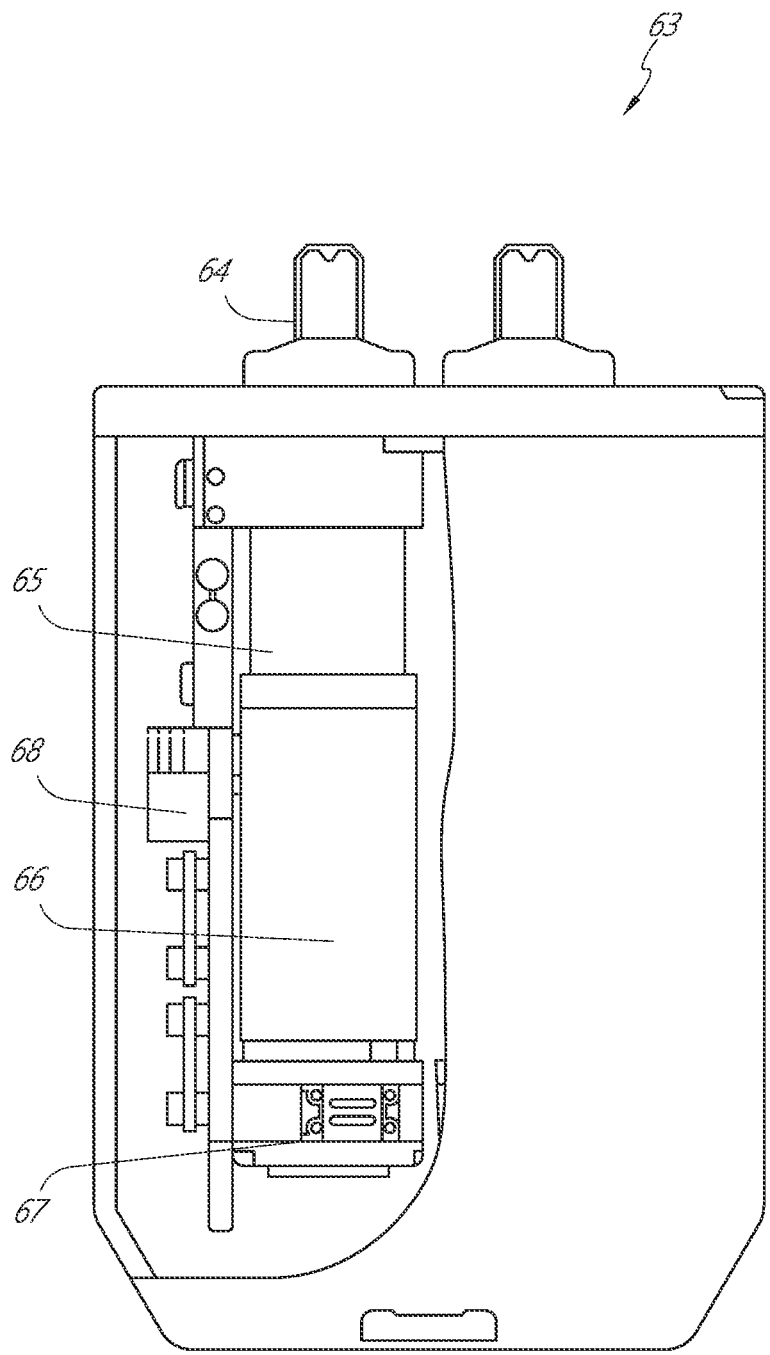
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
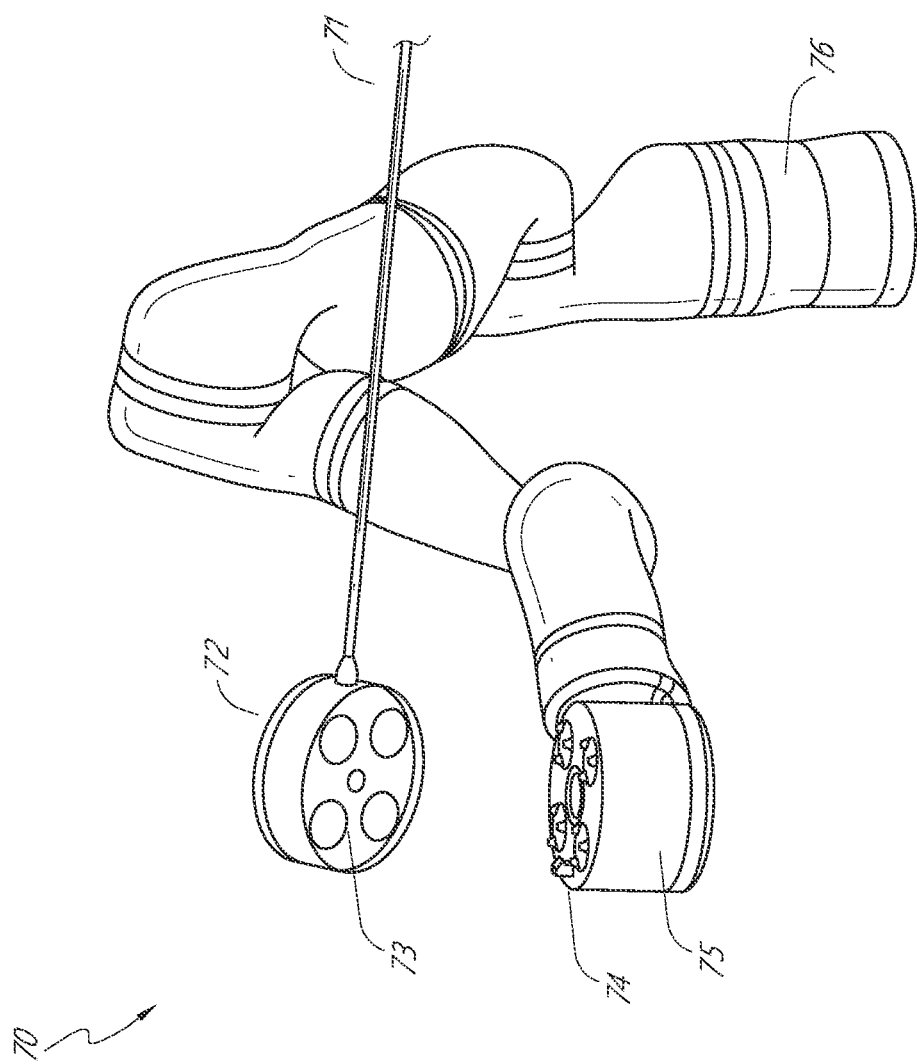
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
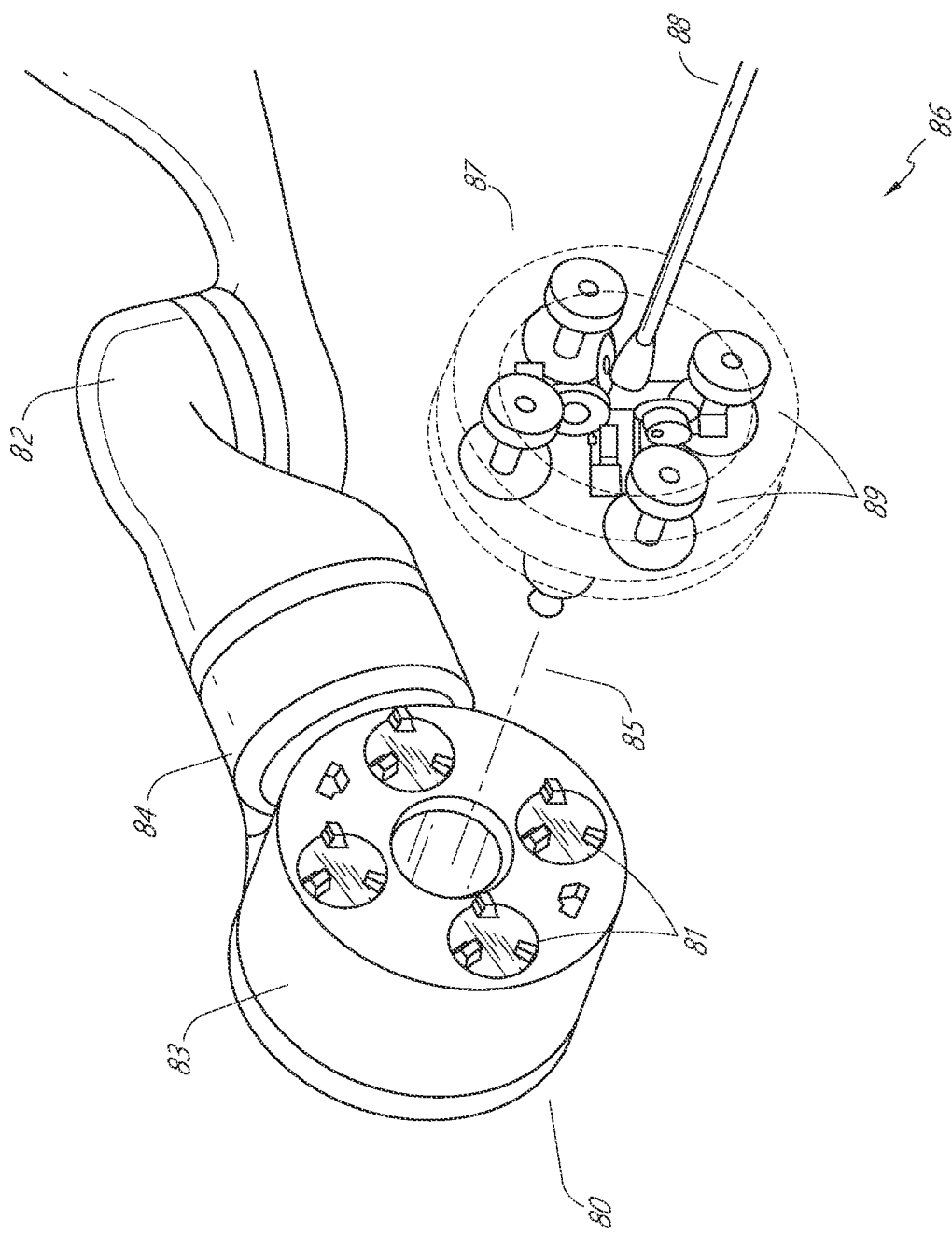
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts and may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
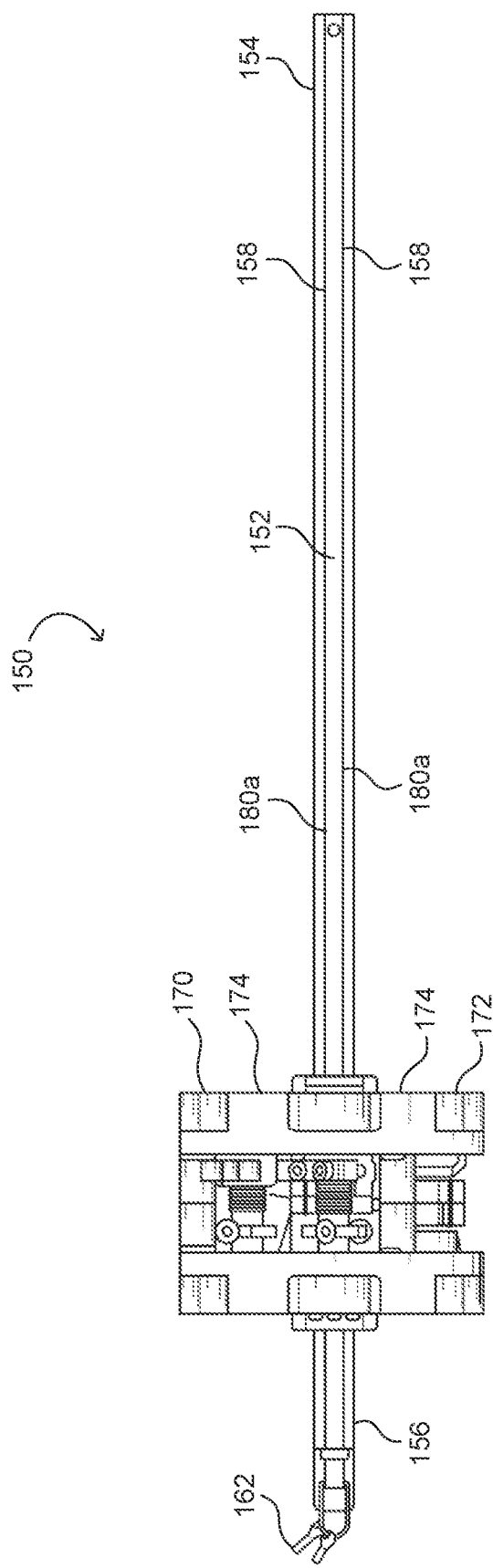
FIG. 18 illustrates an instrument having an instrument-based insertion architecture.

FIG. 18 illustrates an instrument having an instrument-based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
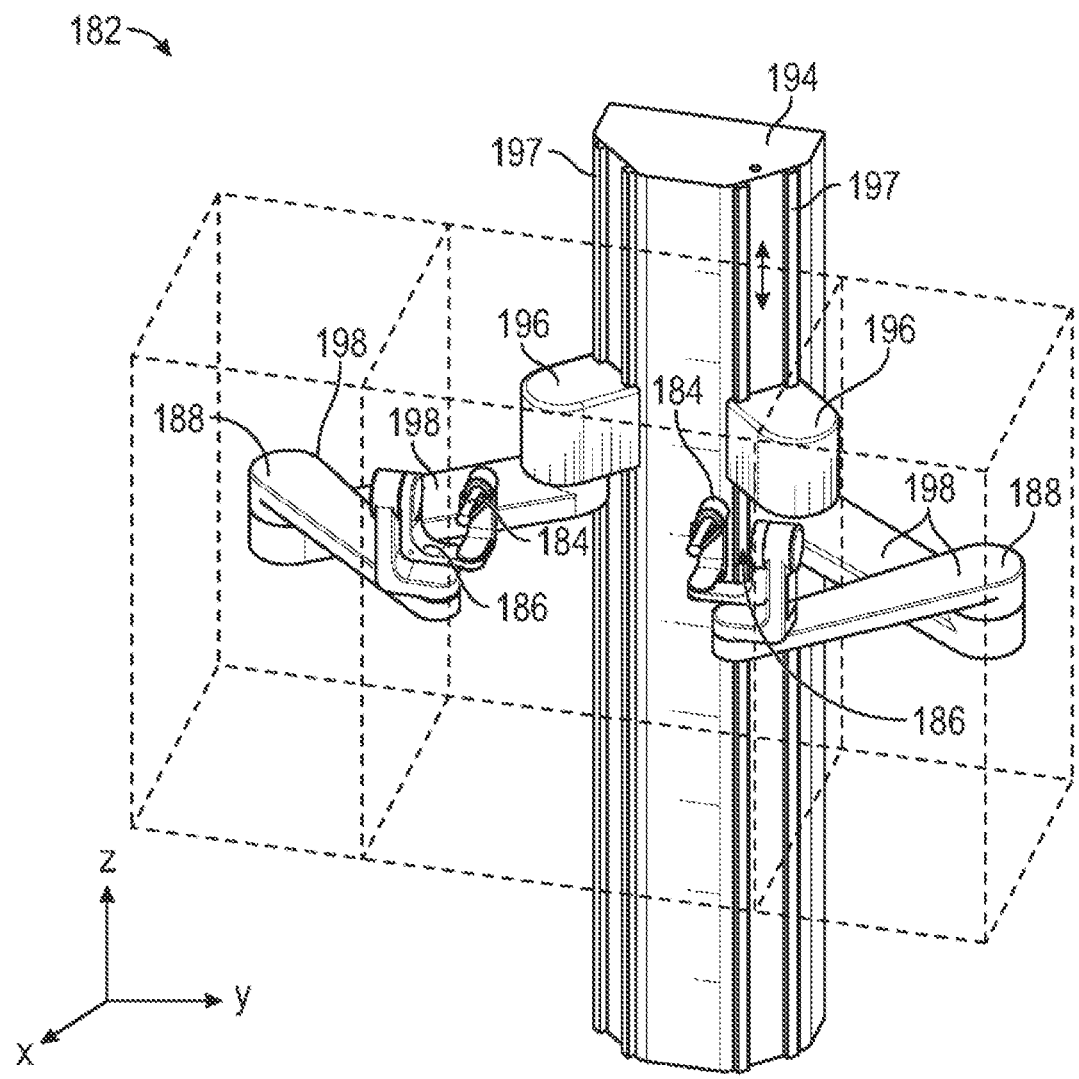
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
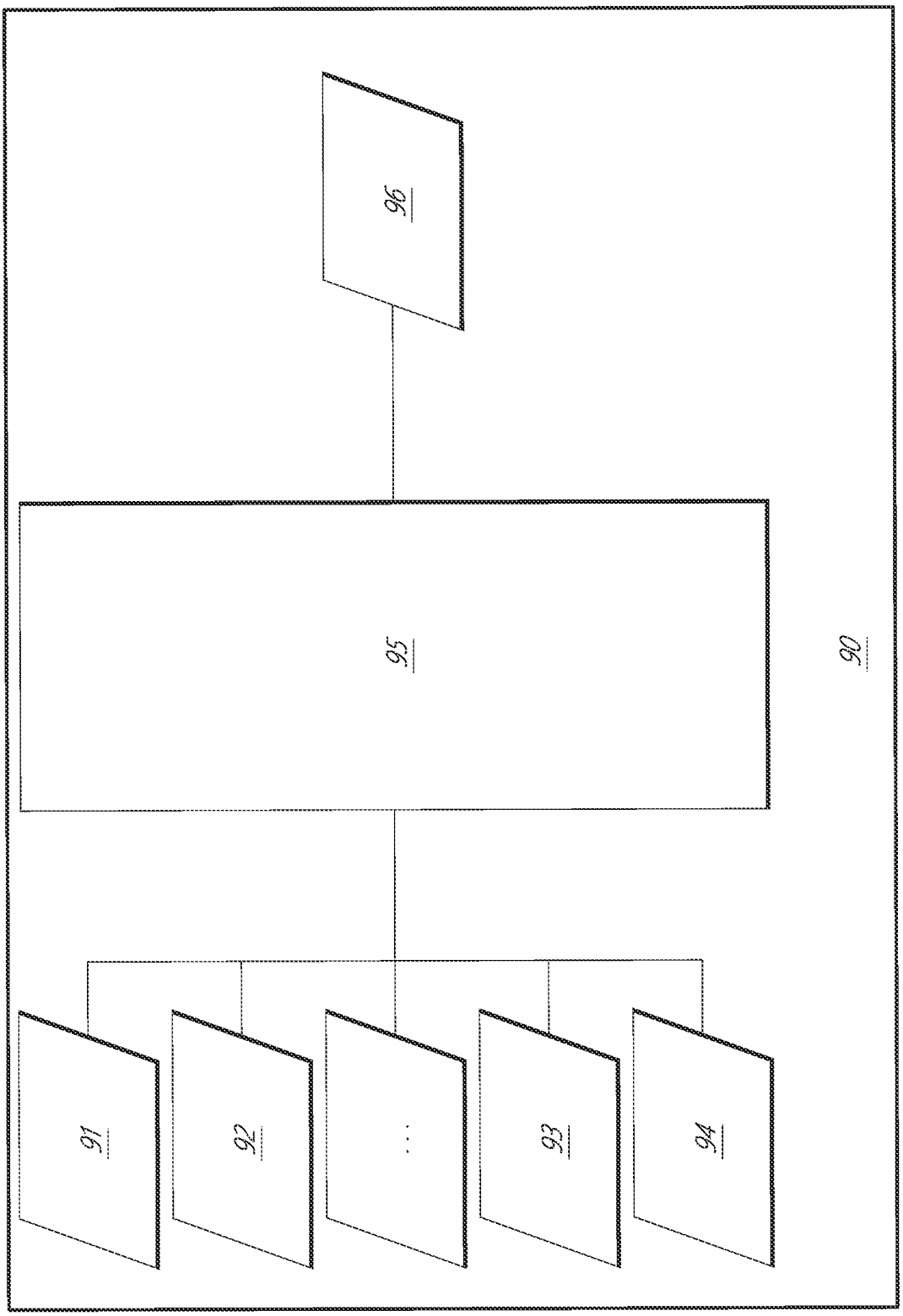
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter) may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the naviga-tional and localization data, such as the position of the instrument within the global coordinate system, anatomical map, etc.

2. High-Stiffness Arm Support.

This application discloses high-stiffness bars that support movable robotic arms. Robotic medical systems with such high-stiffness bars can provide enhanced stability to robotic arms and medical tools coupled to robotic arms, which increases the precision and accuracy in robotic medical procedures.

In some embodiments, the bars have cavities for placing actuators therein.

In some embodiments, the number and the area of openings extending from inside the cavities to outside the cavities are reduced (e.g., a bar may have a single slot for electrical connection from inside a cavity to outside a cavity).

A. Robotic System.

Figure 21:
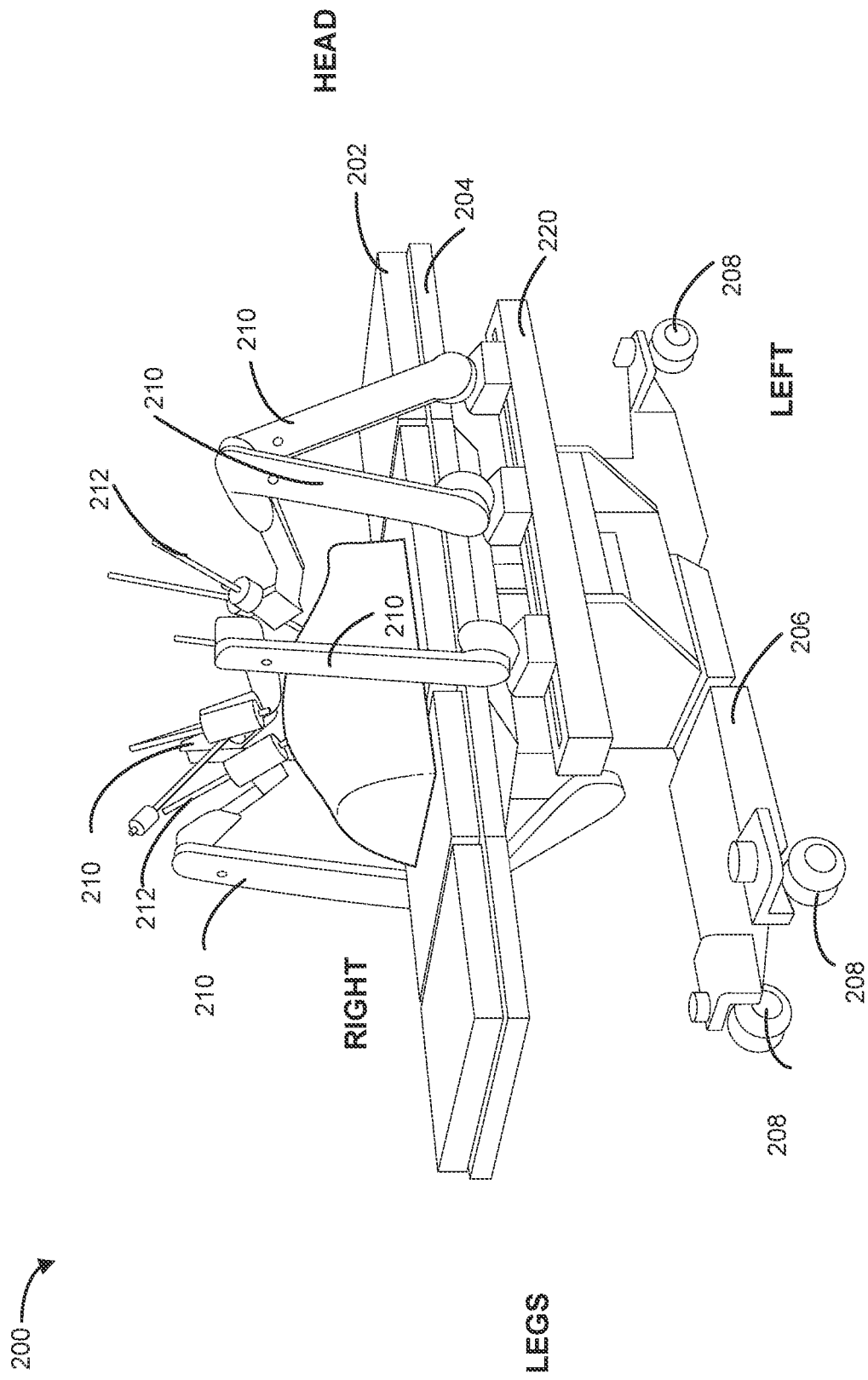
FIG. 21 illustrates an exemplary robotic system according to some embodiments.

FIG. 21 illustrates an exemplary robotic medical system 200 according to some embodiments. In some embodiments, the robotic medical system 200 is a robotic surgery system. In the example of FIG. 21, the robotic medical system 200 comprises a patient support platform 202 (e.g., a patient platform, a table, a bed, etc.). The two ends along the length of the patient support platform 202 are respectively referred to as "head" and "leg". The two sides of the patient support platform 202 are respectively referred to as "left" and "right." The patient support platform 202 includes a support 204 (e.g., a rigid frame) for the patient support platform 202.

The robotic medical system 200 also comprises a base 206 for supporting the robotic medical system 200. The base 206 includes wheels 208 that allow the robotic medical system 200 to be easily movable or repositionable in a physical environment. In some embodiments, the wheels 208 are omitted from the robotic medical system 200 or are retractable, and the base 206 can rest directly on the ground or floor. In some embodiments, the wheels 208 are replaced with feet.

The robotic medical system 200 includes one or more robotic arms 210. The robotic arms 210 can be configured to perform robotic medical procedures as described above with reference to FIGS. 1-20. Although FIG. 21 shows five robotic arms 210, it should be appreciated that the robotic medical system 200 may include any number of robotic arms, including less than five or six or more.

The robotic medical system 200 also includes one or more bars 220 (e.g., adjustable arm support or an adjustable bar) that support the robotic arms 210. Each of the robotic arms 210 is supported on, and movably coupled to, a bar 220, by a respective base joint of the robotic arm. In some embodiments, and as described in FIG. 12, bar 220 can provide several degrees of freedom, including lift, lateral translation, tilt, etc. In some embodiments, each of the robotic arms 210 and/or the adjustable arm supports 220 is also referred to as a respective kinematic chain.

FIG. 21 shows three robotic arms 210 supported by the bar 220 that is in the field of view of the figure. The two remaining robotic arms are supported by another bar that is located across the other length of the patient support platform 202.

In some embodiments, the adjustable arm supports 220 can be configured to provide a base position for one or more of the robotic arms 210 for a robotic medical procedure. A robotic arm 210 can be positioned relative to the patient support platform 202 by translating the robotic arm 210 along a length of its underlying bar 220 and/or by adjusting a position and/or orientation of the robotic arm 210 via one or more joints and/or links (see, e.g., FIG. 24). In some embodiments, the bar pose can be changed via manual manipulation, teleoperation, and/or power assisted motion.

In some embodiments, the adjustable arm support 220 can be translated along a length of the patient support platform 202. In some embodiments, translation of the bar 220 along a length of the patient support platform 202 causes one or more of the robotic arms 210 supported by the bar 220 to be simultaneously translated with the bar or relative to the bar. In some embodiments, the bar 220 can be translated while keeping one or more of the robotic arms stationary with respect to the base 206 of the robotic medical system 200.

In the example of FIG. 21, the adjustable arm support 220 is located along a length of the patient support platform 202. In some embodiments, the adjustable arm support 220 may extend across a partial or full length of the patient support platform 202, and/or across a partial or full width of the patient support platform 202.

During a robotic medical procedure, one or more of the robotic arms 210 can also be configured to hold instruments 212 (e.g., robotically controlled medical instruments or tools, such as an endoscope and/or any other instruments (e.g., sensors, illumination instrument, cutting instrument, etc.) that may be used during surgery), and/or be coupled to one or more accessories, including one or more cannulas, in accordance with some embodiments.

Figure 22:
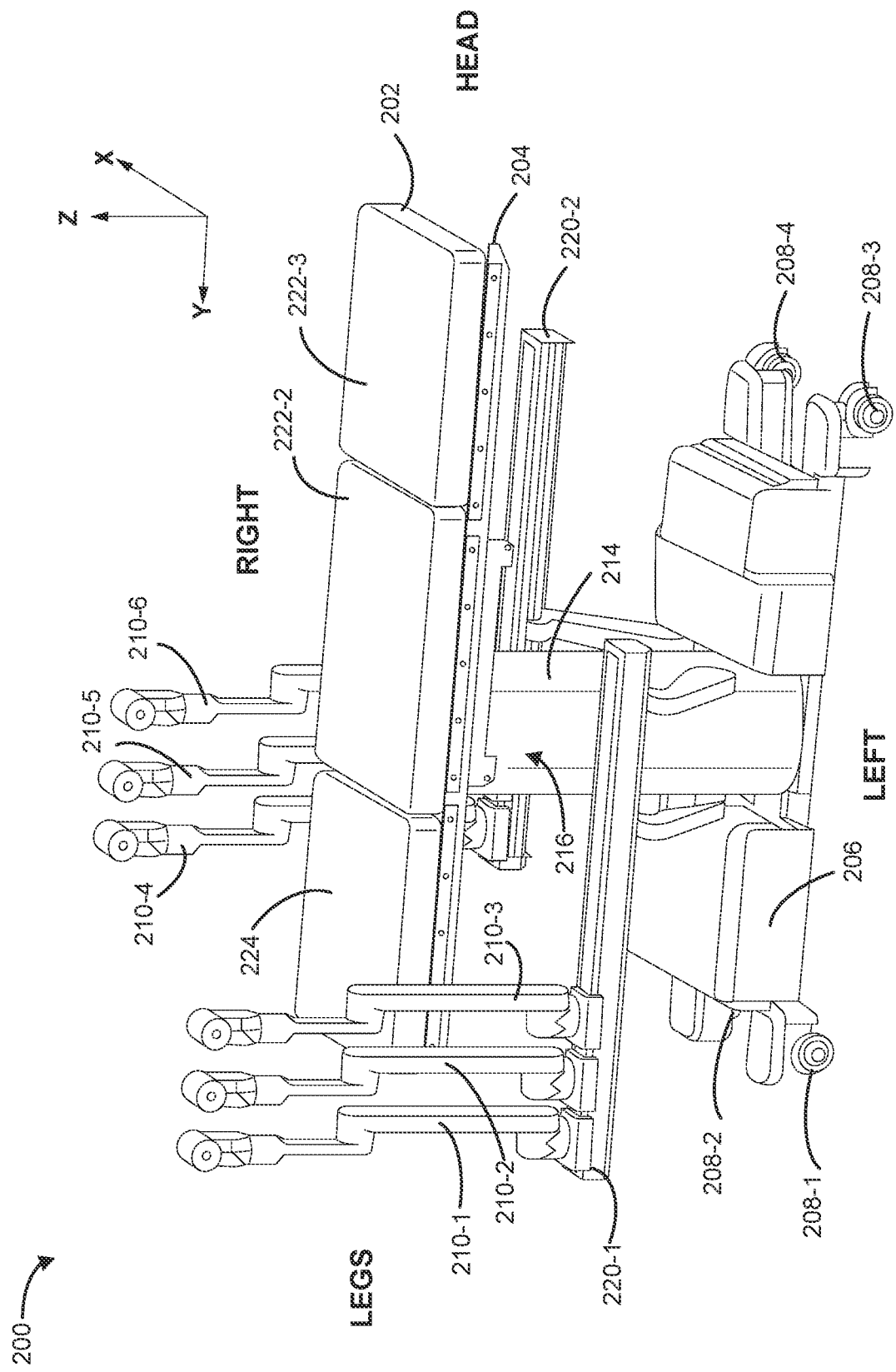
FIG. 22 illustrates another view of an exemplary robotic system according to some embodiments.

FIG. 22 illustrates another view of the exemplary robotic medical system 200 in FIG. 21 according to some embodiments. In this example, the robotic medical system 200 includes six robotic arms 210-1, 210-2, 210-3, 210-4, 210-5, and 210-6. The patient platform 202 is supported by a column 214 that extends between the base 206 and the patient platform 202. In some embodiments, the patient platform 202 comprises a tilt mechanism 216. The tilt mechanism 216 can be positioned between the column 214 and the patient platform 202 to allow the patient platform 202 to pivot, rotate, or tilt relative to the column 214. The tilt mechanism 216 can be configured to allow for lateral and/or longitudinal tilt of the patient platform 202. In some embodiments, the tilt mechanism 216 allows for simultaneous lateral and longitudinal tilt of the patient platform 202.

FIG. 22 shows the patient platform 202 in an untilted state or position. In some embodiments, the untilted state or position is a default position of the patient platform 202. In some embodiments, the default position of the patient platform 202 is a substantially horizontal position as shown in FIG. 22. As illustrated, in the untilted state, the patient platform 202 can be positioned horizontally or parallel to a surface that supports the robotic medical system 200 (e.g., the ground or floor). In some embodiments, the term "untilted" refers to a state in which the angle between the default position and the current position is less than a threshold angle (e.g., less than 5 degrees, or less than an angle that would cause the patient to shift on the patient platform, etc.). In some embodiments, the term "untilted" refers to a state in which the patient platform is substantially perpendicular to the direction of gravity, irrespective of the angle formed by the surface that supports the robotic medical system relative to gravity.

With continued reference to FIG. 22, in the illustrated example of the robotic medical system 200, the patient platform 202 comprises a support 204. In some embodiments, the support 204 includes a rigid support structure or frame, and can support one or more surfaces, pads, or cushions 222. An upper surface of the patient platform 202 can include a support surface 224. During a medical procedure, a patient can be placed on the support surface 224.

FIG. 22 shows the robotic arms 210 and the adjustable arm supports 220 in an exemplary deployed configuration in which the robotic arms 210 reach above the patient platform 202. In some embodiments, due to the configuration of the robotic medical system 200, which enables stowage of different components beneath the patient platform 202, the robotic arms 210 and the arm supports 220 can occupy a space underneath the patient platform 202. Thus, in some embodiments, the tilt mechanism 216 has a low-profile and/or low volume in order to increase the space available for storage below.

FIG. 22 also illustrates an example, x, y, and z coordinate system that may be used to describe certain features of the embodiments disclosed herein. It will be appreciated that this coordinate system is provided for purposes of example and explanation only and that other coordinate systems may be used. In the illustrated example, the x-direction or x-axis extends in a lateral direction across the patient platform 202 when the patient platform 202 is in an untilted state. In some configurations, the x-direction extends across the patient platform 202 from one lateral side (e.g., the right side) to the other lateral side (e.g., the left side) when the patient platform 202 is in an untilted state. The y-direction or y-axis extends in a longitudinal direction along the patient platform 202 when the patient platform 202 is in an untilted state. That is, the y-direction extends along the patient platform 202 from one longitudinal end (e.g., the head end) to the other longitudinal end (e.g., the legs end) when the patient platform 202 is in an untilted state. In an untilted state, the patient platform 202 can lie in or be parallel to the x-y plane, which can be parallel to the floor or ground. In the illustrated example, the z-direction or z-axis extends along the column 214 in a vertical direction. In some embodiments, the tilt mechanism 216 is configured to laterally tilt the patient platform 202 by rotating the patient platform 202 about a lateral tilt axis that is parallel to the y-axis. The tilt mechanism 216 can further be configured to longitudinally tilt the patient platform 202 by rotating the patient platform 202 about a longitudinal tilt axis that is parallel to the x-axis.

B. Arm Support.

As described with respect to FIG. 12, the bar 220 (e.g., adjustable arm support) can provide several degrees of freedom, including translation of robotic arms, in addition to lift, lateral translation, tilt, etc. of the bar 220. Thus, depending on the embodiment, a robotic medical system can have many more robotically controlled degrees of freedom beyond just those in the robotic arms 210 to provide for null space movement and collision avoidance. In a respective embodiment of these embodiments, the end effectors of one or more robotic arms (and any tools or instruments coupled thereto) and a remote center along the axis of the tool can advantageously maintain in pose and/or position within a patient.

As described above, a bar 220 with high stiffness can enhance the stability of the robotic arms 210 supported by the bar 220.

Figure 23:
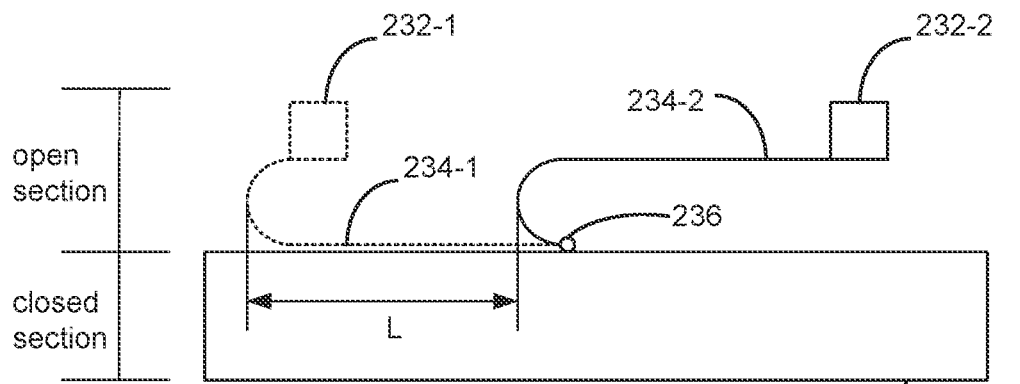
FIG. 23 illustrates an example configuration of a bar.

FIG. 23 illustrates an example configuration of a bar 230. In FIG. 23, the bar 230 includes a closed section and an open section, where a carriage 232 is located in the open section of the bar 230. The carriage 232 is moveable between two locations 232-1 and 232-2 shown in FIG. 23, and supports a robotic arm (e.g., a lateral movement of the carriage 232 causes translation of the robotic arm relative to the bar 230). In order not to obscure other aspects shown in FIG. 23, an actuator for moving the carriage 232 is not shown in FIG. 23.

The carriage 232 is electrically coupled to an electrode 236 at a fixed location via an electrical cable 234, which may provide electrical power and/or control signals. The electrical cable 234 may also transmit sensor signals from one or more sensors located in a robotic arm. In FIG. 23, the electrical cable 234 includes a rolling loop (e.g., a rolling bend). The rolling loop of the electrical cable 234 may sweep a distance L (from the electrical cable 234 in a first position 234-1 when the carriage 232 is at location 232-1 to the electrical cable 234 in a second position 234-2 when the carriage 232 is at location 232-2) when the carriage 232 travels the distance 2L between the two locations 232-1 and 232-2. Thus, the configuration shown in FIG. 23 requires the open section of the bar 230 to extend at least half of the travel of the carriage 232 for the sweeping of the electrical cable 234.

Figure 24:
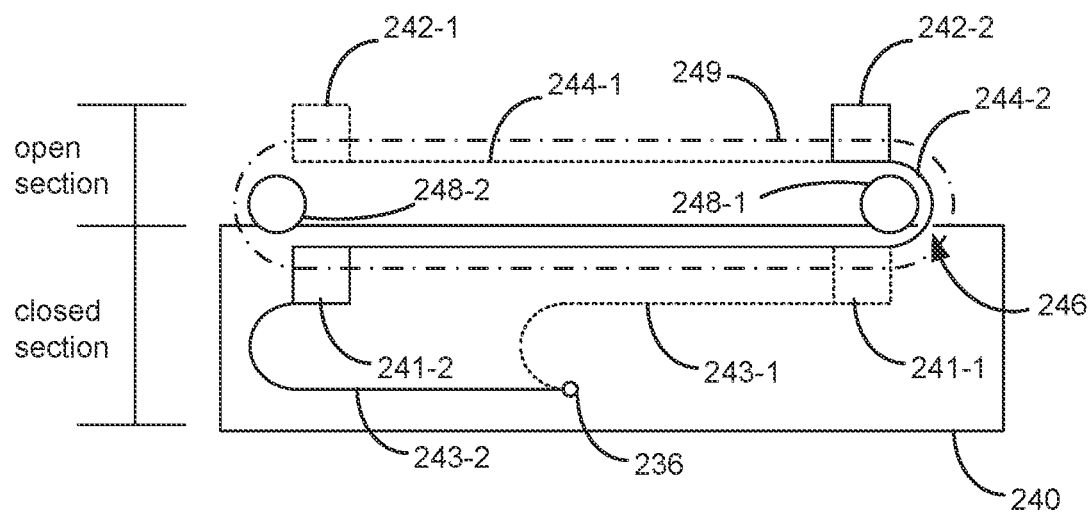
FIG. 24 illustrates movement of a carriage according to some embodiments.

In comparison, the bar 240 shown in FIG. 24 includes a carriage 241 (called an intermediate carriage in this configuration) and an electrical cable 243 located in the closed section of the bar 240 (e.g., inside a cavity of the bar 240). Although the carriage 241 and the electrical cable 243 operate similarly to the carriage 232 and the electrical cable 234 shown in FIG. 23 (e.g., the electrical cable 243 has a rolling loop so that the electrical cable 243 is in a first position 243-1 when the carriage 241 is at location 241-1 and the electrical cable 243 is in a second position 243-2 when the carriage 241 is at location 241-2), placing the carriage 232 and the electrical cable 234 in the closed section of the bar 240 allows a larger portion of the bar 240 to be used as the closed section compared to the bar 230.

However, because the carriage 241 is located in the closed section of the bar 240, a robotic arm may be mounted on a carriage 242 that is located outside the closed section of the bar 240. The carriage 242 is electrically coupled to the carriage 241 via an electrical cable 244. By moving the carriage 241 and the carriage 242 synchronously, the electrical cable 244 maintains the electrical connection between the carriage 241 and the carriage 242. For example, placing the carriage 241 at location 241-1 when the carriage 242 is at location 242-1 allows the electrical cable 244 in position 244-1 to provide electrical connection between the carriage 241 and the carriage 242, and placing the carriage 241 at location 241-2 when the carriage 242 is at location 242-2 allows the electrical cable 244 in position 244-2 to provide electrical connection between the carriage 241 and the carriage 242.

This configuration also requires a single opening 246 (e.g., a slot) for allowing the electrical cable 244 from inside the closed section to outside the closed section. In comparison to the configuration shown in FIG. 23, which requires an area for sweeping of the electrical cable at least half of the travel of the carriage, the configuration shown in FIG. 24 can have higher stiffness. In particular, the size of the opening 246 does not depend on the travel of the carriage, and thus, the configuration shown in FIG. 24 would be particularly beneficial when a long travel of the carriage is required.

In some embodiments, the carriage 241 and the carriage 242 have separate actuators (e.g., the carriage 241 has a first actuator and the carriage 242 has a second actuator that is distinct and separate from the first actuator), and the separate actuators are controlled to provide synchronous movements. In some embodiments, the carriage 241 and the carriage 242 are coupled (directly or indirectly) to a common actuator. For example, the carriage 241 and the carriage 242 may be coupled to a common mechanical component (e.g., a mechanical band 249, such as a steel or tungsten band) so that the movements of the carriage 241 and the carriage 242 are mechanically synchronized. In some embodiments, the bar 240 includes one or more pulleys 248-1 and/or 248-2 for guiding rolling movement of the mechanical band 249 and/or the electrical cable 244.

Figure 25A:
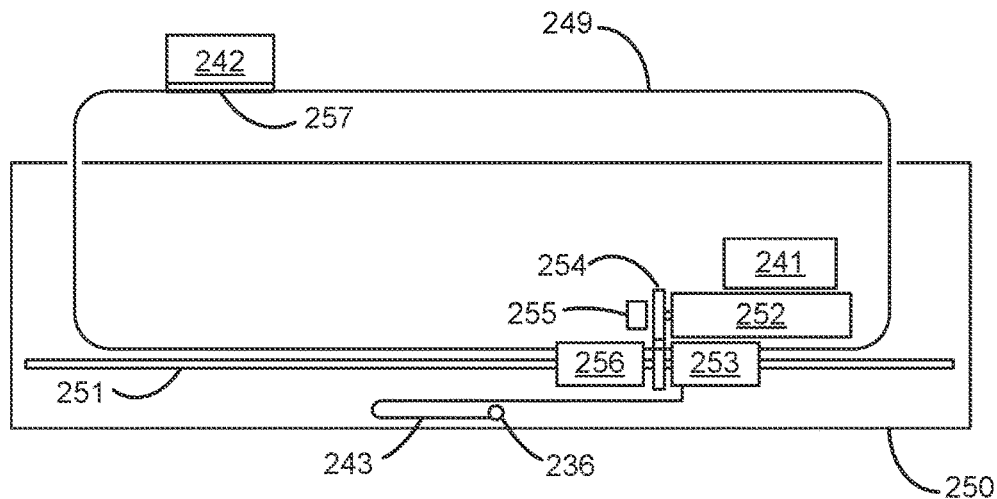
FIG. 25A illustrates an arm support configured for moving a robotic arm, in accordance with some embodiments.

FIG. 25A illustrates an arm support 250 configured for moving a robotic arm, in accordance with some embodiments.

The arm support 250 includes a ball screw 251 and a ball nut 253 rotationally coupled onto the ball screw 251. The arm support 250 also includes a motor 252 coupled with the ball nut 253 (e.g., via one or more gears 254) to rotate the ball nut 253 so that the ball nut 253 (and other components coupled to the ball nut 253) may move along the ball screw 251 relative to the ball screw 251. Although FIG. 25A shows the motor 252 positioned offset from the ball screw 251, in some embodiments, the motor 252 may be positioned on-axis with the ball screw 251.

In some embodiments, the arm support 250 includes a sensor (e.g., an encoder, a position sensor, etc.) for determining the position of the motor 252. In some embodiments, the arm support 250 also includes a brake 256 for stopping the movement of the motor 252, the ball nut 253, and/or the gears 254. In some embodiments, the carriage 242 is coupled with a sensor 257 (e.g., a force sensor) for determining one or more forces applied to the carriage 242. In some embodiments, the motor 252 is coupled to, or is part of, the carriage 241. In some embodiments, the carriage 241 also includes electronics for receiving information from one or more sensors (e.g., encoder 255, sensor 257, etc.) and/or activating the motor 252 and/or the brake 256.

The arm support 250 includes the mechanical band 249 for providing a tension to the carriage 242 so that the carriage 242 may move (e.g., along a track).

FIG. 25A also shows that the carriage 241 may be electrically coupled to the electrode 236 at a fixed location (e.g., via the electrical cable 243).

As described with respect to FIG. 24, the carriage 241 may be electrically coupled to the carriage 242 (e.g., via the electrical cable 244). For brevity, such details are not repeated herein.

Figure 25B:
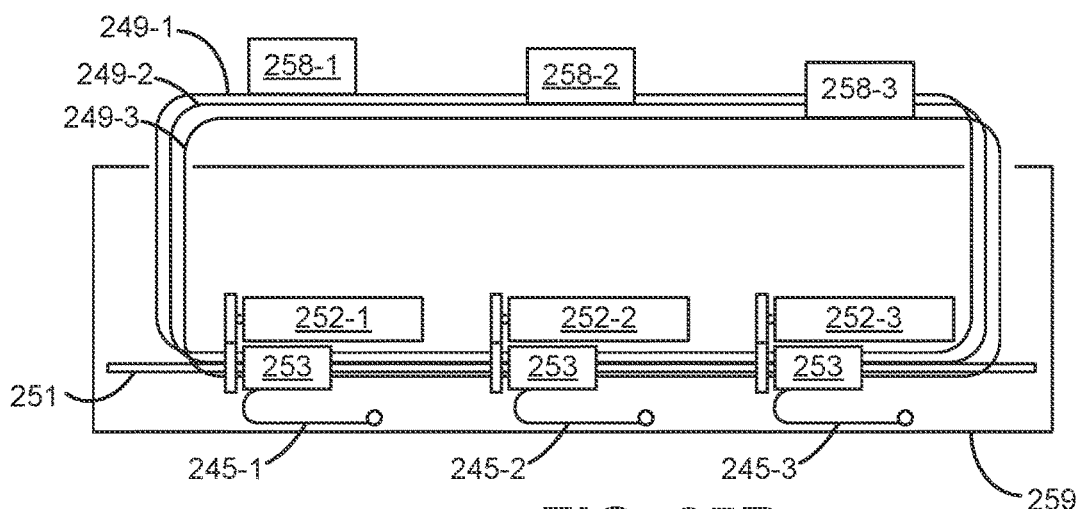
FIG. 25B illustrates an arm support configured for moving multiple robotic arms, in accordance with some embodiments.

FIG. 25B illustrates an arm support 259 configured for moving multiple robotic arms, in accordance with some embodiments. The arm support includes three carriages 258-1, 258-2, and 258-3 for supporting three robotic arms (e.g., the carriage 258-1 may support a first robotic arm, the carriage 258-2 may support a second robotic arm, and the carriage 258-3 may support a third robotic arm). The arm support 259 includes three motors 252-1, 252-2, and 252-3, which are coupled to the carriages 258-1, 258-2, and 258-3 via mechanical bands 249-1, 249-2, and 249-3, respectively so that the carriages 258-1, 258-2, and 258-3 may be moved independently from one another.

In FIG. 25B, the motors 252-1, 252-2, and 252-3 are electrically coupled to electrodes via cables 245-1, 245-2, and 245-3, each of which includes a rolling loop.

Figure 26:
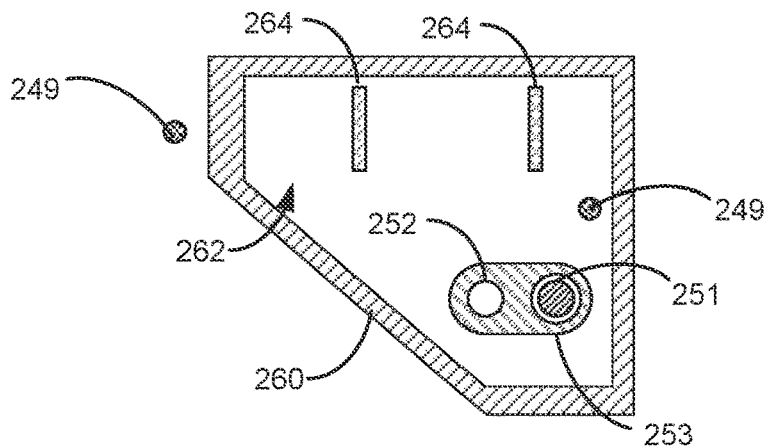
FIG. 26 illustrates a cross-section of an arm support in accordance with some embodiments.

FIG. 26 illustrates a section of the arm support in accordance with some embodiments. In FIG. 26, the arm support includes a shell 260 defining a closed section 262. The shell 260 may have a shape of a tube (e.g., a circular or rectangular tube) or any other tubular shape. The arm support also includes an electrical cable 264 (in a rolled configuration as shown in FIG. 24 so that the sectional view shown in FIG. 26 shows two portions of the same electrical cable 264). The arm support may further include the ball screw 251, the ball nut 253, and the motor 252 within the closed section 262. In FIG. 26, one portion of the mechanical band 249 (or wire) is located within the closed section 262 and another portion of the mechanical band 249 (or wire) is located outside the closed section 262, similarly to the mechanical band 249 shown in FIG. 25A.

Thus, the torsional stiffness of the arm support is increased by placing the actuator (e.g., a combination of the ball screw 251, the ball nut 253, and the motor 252) inside the closed section 262.

In view of the principles and examples described herein, some embodiments of the present disclosure are described below.

In accordance with some embodiments, a surgical system (e.g., a robotic medical system, a robotic surgery platform, etc., such as the robotic medical system 200) includes an elongated arm support (e.g., arm support 220-1 shown in FIG. 22) and a first robotic arm (e.g., robotic arm 210-1 shown in FIG. 22) supported on the elongated arm support (e.g., the robotic arm 210-1 may be supported by the carriage 258-1 shown in FIG. 25A). For example, the first robotic arm may move relative to the elongated arm support, such as translating relative to the elongated arm support). A partially enclosed (hollow) cavity is defined in the elongated arm support (e.g., the elongated arm support may have a closed section, such as the closed section 262, for a substantial length of the elongated arm support, and also have one or more openings for allowing an electrical cable to extend from inside the cavity to outside the cavity) for receiving a first electrical cable electrically coupled (directly or indirectly) to the first robotic arm so that the first electrical cable is within the cavity and includes a first rolling loop that moves in conjunction with movement of the first robotic arm. For example, as shown in FIG. 24, when the carriage 242 supporting a robotic arm is at location 242-1, the electrical cable 243 with a rolling loop is in the first position 243-1 and when the carriage 242 supporting the robotic arm is at location 242-2, the electrical cable 243 with the rolling loop is in the second position 243-2. As shown in FIG. 24, the position of the rolling loop (e.g., bend) changes as the first robotic arm or the carriage 242 supporting the first robotic arm moves. In some embodiments, as shown in FIG. 24, the first electrical cable remains entirely within the cavity.

In some embodiments, the surgical system includes a first actuator (e.g., motor 252 shown in FIG. 25A) located within the cavity. The first electrical cable is coupled to the first actuator (e.g., as shown in FIG. 24, the first electrical cable 243 is coupled to the intermediate carriage 241, which may include the first actuator).

In some embodiments, the first actuator is a linear actuator (e.g., a mechanical linear actuator, a hydraulic liner actuator, a pneumatic linear actuator, a piezoelectric linear actuator, an electro-mechanical linear actuator, etc.).

In some embodiments, the first actuator is coupled to a ball screw. For example, as shown in FIG. 25A, the first actuator may include the ball nut 253 coupled with the motor 252. The ball nut 253 may be coupled with the ball screw 251 so that rotating the ball nut 253 (or the ball screw 251) causes lateral movement of the ball nut 253 (and components coupled to the ball nut 253) relative to the ball screw 251.

In some embodiments, the ball screw is immobilized relative to the elongated arm support. The first actuator is movable relative to the elongated arm support within the cavity. For example, in FIG. 25A, the ball screw 251 is fixed in position relative to the arm support 250. In such configurations, rotating the ball nut 253 with the motor 252 causes movement of the motor 252 along the ball screw 251.

In some embodiments, the surgical system includes a carriage (e.g., the carriage 242 shown in FIG. 25A) located outside the cavity. The carriage is coupled with the first robotic arm, and the first actuator is (e.g., mechanically) connected to the carriage for moving the carriage and the first robotic arm along the elongated arm support.

In some embodiments, the first actuator is connected to the carriage via a second electrical cable (e.g., the electrical cable 244 shown in FIG. 24) that is distinct from the first electrical cable.

In some embodiments, the second electrical cable is in the form of a pull-pull cable (e.g., the second electrical cable is configured to support a tensile force).

In some embodiments, an opening (e.g., holes, slots, notches, etc.) in communication with the cavity is defined in the elongated arm support (e.g., the opening 246 shown in FIG. 24). The second electrical cable is arranged to extend from inside the cavity to outside the cavity through the opening.

In some embodiments, the first actuator is connected to the carriage via a transmission band (e.g., the transmission band 249 shown in FIG. 25A).

In some embodiments, the transmission band includes stainless steel or tungsten.

In some embodiments, the second electrical cable includes the transmission band (e.g., the second electrical cable may be formed to include one or more components for supporting tensile strength). In some embodiments, the second electrical cable is coupled with the transmission band (e.g., the second electrical cable may be attached to the transmission, which is configured for supporting tensile strength).

In some embodiments, the second electrical cable is electrically coupled to the first robotic arm via the carriage (e.g., the second electrical cable 244 is electrically coupled to the carriage 242, which is, in turn, electrically coupled with a robotic arm so that the second electrical cable 244 is electrically coupled (indirectly via the carriage 242) to the robotic arm supported by the carriage 242).

In some embodiments, the first actuator is electrically coupled to an electrode positioned at a fixed location relative to the elongated arm support via the first electrical cable (e.g., the carriage 241 shown in FIG. 24 is electrically coupled to the electrode 236 via the first electrical cable 243).

In some embodiments, the surgical system includes a second robotic arm (e.g., the robotic arm 210-2, which may be supported on the carriage 258-2), distinct and separate from the first robotic arm, supported on the elongated arm support. A third electrical cable (e.g., electrical cable 245-2) electrically coupled (directly or indirectly) to the second robotic arm is located within the cavity and the third electrical cable includes a second rolling loop that moves in conjunction with movement of the second robotic arm.

In some embodiments, the surgical system includes a second actuator (e.g., motor 252-2) located within the cavity. The third electrical cable is coupled to the second actuator.

In some embodiments, the surgical system includes a third robotic arm (e.g., the robotic arm 210-3, which may be supported on the carriage 258-3), distinct and separate from the first robotic arm and the second robotic arm, supported on the elongated arm support. A fourth electrical cable (e.g., electrical cable 245-3) electrically coupled (directly or indirectly) to the third robotic arm is located within the cavity and the fourth electrical cable includes a third rolling loop that moves in conjunction with movement of the third robotic arm.

In some embodiments, the surgical system includes a third actuator (e.g., motor 252-3) located within the cavity. The fourth electrical cable is coupled to the third actuator.

In some embodiments, the first actuator, the second actuator, and the third actuator are coupled to a common ball screw (e.g., FIG. 25B).

In some embodiments, the surgical robotic system is a bed-based system (e.g., the surgical robotic system includes a bed or a patient support platform 202, as illustrated in FIG. 21 and FIG. 22). The first robotic arm and the elongated arm support are integrated into the bed-based system.

In some embodiments, the surgical robotic system further includes a second arm support (e.g., adjustable arm support 220-2 shown in FIG. 22) and a second robotic arm supported (e.g., movably coupled to) via the second arm support (e.g., robotic arm 210-4).

In accordance with some embodiments, a surgical system (e.g., a robotic medical system, a robotic surgery platform, etc., such as the robotic medical system 200) includes an elongated arm support (e.g., arm support 220-1) and a robotic arm (e.g., robotic arm 210-1) supported on the elongated arm support. A partially enclosed cavity is defined in the elongated arm support for receiving an actuator and an electrical cable therein so that the first electrical cable is within the cavity and includes a rolling loop that moves in conjunction with movement of the robotic arm. For example, as shown in FIG. 24, the position of the rolling loop (e.g., bend) changes as the robotic arm or the carriage 242 supporting the robotic arm moves.

In accordance with some embodiments, a surgical system (e.g., a robotic medical system, a robotic surgery platform, etc., such as the robotic medical system 200) includes a beam (e.g., arm support) with a partially enclosed cavity defined therein, a first carriage (e.g., carriage 241) located within the cavity, a second carriage (e.g., carriage 242) located at least partially outside the cavity, and an actuator located within the cavity (e.g., motor 252). The actuator is mechanically coupled with the first carriage and the second carriage by a band or wire (e.g., band 249) for moving the first carriage and the second carriage. The surgical system also includes a first electrical cable (e.g., electrical cable 243) with a rolling loop for electrically coupling the first carriage from a fixed point within the cavity and a second electrical cable (e.g., electrical cable 244) electrically coupling the first carriage and the second carriage.

In accordance with some embodiments, a surgical system includes a joint. The joint includes a chassis (e.g., a frame of the arm support, such as the shell 260) with an enclosed cavity and a load-bearing output carriage (e.g., the first carriage that supports a robotic arm, such as the carriage 242), which moves relative to the chassis. The joint also includes an electrical cable assembly (e.g., a combination of the electrical cable 243 and the electrical cable 244) coupled to both the chassis and the load-bearing output carriage. The electrical cable assembly has a first bend (e.g., rolling loop, such as a bend between the electrode 236 and the carriage 241 as shown in FIG. 24) located within the enclosed cavity which moves relative to the chassis as the load-bearing output carriage moves. The electrical cable assembly has a second bend (e.g., a bend between the carriage 241 and the carriage 242) around a redirect surface (e.g., a static surface or pulley). The second bend does not move relative to the chassis.

In some embodiments, the joint is prismatic (e.g., a joint that provides a linear sliding movement between two objects). A prismatic joint may be called a slider.

In some embodiments, the enclosed cavity extends along a majority of the length of the chassis. For example, the enclosed cavity extends along at least 50%, 60%, 70%, 80%, 90%, 95%, or 99% of the length of the chassis, or within a range between any two of the aforementioned percentage values.

In some embodiments, the cavity is partially enclosed (e.g., the cavity is fully enclosed except for an opening that allows a portion of the electrical cable assembly to provide electrical connection between inside the cavity and outside the cavity.

In some embodiments, an intermediate carriage (e.g., carriage 241) is located inside the enclosed cavity. The intermediate carriage is coupled to the electrical cable assembly between the first bend and the second bend (e.g., FIG. 24).

In some embodiments, the intermediate carriage (e.g., carriage 241) is coupled to the load-bearing output carriage with a flexible tensile member (e.g., band or wire) and configured such that the motion of the intermediate carriage and the load-bearing output carriage are synchronized.

In some embodiments, the intermediate carriage includes an actuator (e.g., the motor 252).

3. Implementing Systems and Terminology.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for controlling arm supports, robotic arms, and associated actuators may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the term "exemplary" means "serving as an example, instance, or illustration," and does not necessarily indicate any preference or superiority of the example over any other configurations or implementations.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the embodiments shown herein but is to be accorded the widest scope consistent with the principles and novel features disclosed herein.

What is claimed is:

1. A surgical system, comprising:
an elongated arm support;
a first robotic arm supported on the elongated arm support, wherein a partially enclosed cavity is defined in the elongated arm support for receiving a first electrical cable so that the first electrical cable is within the cavity and includes a first rolling loop that moves in conjunction with movement of the first robotic arm;
a carriage located outside the cavity, wherein the carriage is coupled with the first robotic arm; and
a first actuator located within the cavity,
wherein the first actuator is electrically coupled to an electrode positioned at a fixed location relative to the elongated arm support via the first electrical cable,
wherein the first actuator is connected to the carriage for moving the carriage and the first robotic arm along the elongated arm support,
wherein the first actuator is connected to the carriage via a second electrical cable that is distinct from the first electrical cable.

2. The surgical system of claim 1, wherein the first actuator is a linear actuator.

3. The surgical system of claim 1, wherein the first actuator is coupled to a ball screw.

4. The surgical system of claim 3, wherein:
the ball screw is immobilized relative to the elongated arm support; and
the first actuator is movable relative to the elongated arm support within the cavity.

5. The surgical system of claim 1, wherein:
an opening in communication with the cavity is defined in the elongated arm support; and
the second electrical cable is arranged to extend from inside the cavity to outside the cavity through the opening.

6. The surgical system of claim 1, wherein:
the first actuator is connected to the carriage via a transmission band; and
the transmission band includes stainless steel or tungsten.

7. The surgical system of claim 6, wherein the second electrical cable includes the transmission band or is coupled with the transmission band.

8. The surgical system of claim 1, further comprising:
a second robotic arm supported on the elongated arm support,
wherein a third electrical cable electrically coupled to the second robotic arm is located within the cavity and includes a second rolling loop that moves in conjunction with movement of the second robotic arm.

9. The surgical system of claim 8, further comprising:
a third robotic arm supported on the elongated arm support,
wherein a fourth electrical cable electrically coupled to the third robotic arm is located within the cavity and includes a third rolling loop that moves in conjunction with movement of the third robotic arm.

10. The surgical system of claim 1, wherein the first actuator is included in an intermediate carriage that is configured to move synchronously with the carriage that is coupled to the first robotic arm.

11. The surgical system of claim 10, wherein the second electrical cable maintains an electrical connection between the intermediate carriage and the carriage that is coupled to the first robotic arm.

12. The surgical system of claim 1, wherein the second electrical cable extends through a single opening in the arm support.

13. The surgical system of claim 1, wherein the elongated arm support is in the form of a bar.

14. The surgical system of claim 1, wherein the elongated arm support is mounted to a patient table.

* * * * *